United States Patent
Casbolt et al.

(10) Patent No.: US 11,242,358 B2
(45) Date of Patent: Feb. 8, 2022

(54) METAL ION COMPLEXES

(71) Applicant: RR Medsciences Pty Ltd., Gordon (AU)

(72) Inventors: Llewellyn Stephen Frank Casbolt, Mount Rankin (AU); William John Simpson, Woodrising (AU)

(73) Assignee: RR Medsciences Pty Ltd., Gordon (AU)

( * ) Notice: Subject to any disclaimer, the term of this patent is extended or adjusted under 35 U.S.C. 154(b) by 0 days.

(21) Appl. No.: 16/720,864

(22) Filed: Dec. 19, 2019

(65) Prior Publication Data

US 2020/0299310 A1 Sep. 24, 2020

Related U.S. Application Data

(62) Division of application No. 15/738,035, filed as application No. PCT/AU2016/050518 on Jun. 17, 2016, now Pat. No. 10,550,132.

(30) Foreign Application Priority Data

Jun. 19, 2015 (AU) ................. 2015902374

(51) Int. Cl.
  *C07F 1/00* (2006.01)
  *A61K 33/34* (2006.01)
  *A61K 9/00* (2006.01)
  *A61P 17/02* (2006.01)
  *A61P 25/00* (2006.01)
  *A61P 35/00* (2006.01)

(52) U.S. Cl.
  CPC ............ *C07F 1/005* (2013.01); *A61K 9/0014* (2013.01); *A61K 33/34* (2013.01); *A61P 17/02* (2018.01); *A61P 25/00* (2018.01); *A61P 35/00* (2018.01)

(58) Field of Classification Search
  CPC ............ C07F 1/005; A61P 17/02; A61P 25/00
  See application file for complete search history.

(56) References Cited

U.S. PATENT DOCUMENTS 7,666,390 B2 * 2/2010 Hong ................. A61K 49/0438
                                                           424/1.45
2008/0064211 A1  3/2008 Tsugita et al.

FOREIGN PATENT DOCUMENTS

AU  2004205086 A1  3/2006
CA     2478137 A1  2/2006

OTHER PUBLICATIONS

International Search Report dated Aug. 29, 2016, issued in connection with International Patent Application No. PCT/AU2016/050518 (6 pages).

* cited by examiner

*Primary Examiner* — Pancham Bakshi
(74) *Attorney, Agent, or Firm* — McNeill Baur PLLC

(57) ABSTRACT

The present invention provides a process for the preparation of metal ion complexes, the process comprising contacting a metal in the form of particles with a chelating agent in solid form and, while the metal is in contact with the chelating agent, contacting the metal and chelating agent with an oxidising agent. The present invention also provides novel metal ion complexes. The invention further provides uses of the metal ion complexes.

10 Claims, 7 Drawing Sheets

METAL ION COMPLEXES

CROSS-REFERENCE TO RELATED APPLICATIONS

This application is a division of U.S. application Ser. No. 15/738,035 filed Dec. 19, 2017, which is a U.S. National Stage Entry of International Patent Application Serial No. PCT/AU2016/050518 filed Jun. 17, 2016, which claims the benefit of Australian Patent Application No. 2015902374 filed Jun. 19, 2015, each of which is incorporated by reference herein in their entireties.

FIELD OF THE INVENTION

The present invention relates to metal ion complexes, a process for the preparation of metal ion complexes, compositions comprising metal ion complexes and the uses thereof.

BACKGROUND

Metals, metal ions and their complexes play an important physiological role in animals, humans and plants. For example, metals such as copper, zinc, iron, calcium and the like, are important for, among other things, bone development, energy production and fatty acid oxidation. In addition, metals may be incorporated into enzymes and proteins, and may also function as co-factors (for example, copper is a co-factor associated with the enzyme superoxide dismutase).

Administration of metal ions and their complexes can be therapeutically useful. For example, metal ions, such as copper ions, have been administered in the form of salts, such as, for example, metal sulfides, chlorides and nitrates, for various therapeutic uses.

The specification for Australian patent application no. 2004205096 (AU 2004205066 A1) discloses a process for preparing a metal ion chelate complex. This document discloses a process for preparing copper EDTA and related complexes, involving mixing a chelating agent with an oxidising agent in solution to obtain a mixture and adding at least one metal capable of forming a metal ion chelate complex with said chelating agent to said mixture, so as to form at least one metal ion chelate complex, or a mixture thereof.

It would be advantageous to provide metal ion complexes with different and/or new structures. It would also be advantageous to provide alternative processes for preparing metal ion complexes.

SUMMARY OF THE INVENTION

The present inventors have developed a novel process for preparing metal ion complexes, novel metal ion complexes, and methods of using such complexes.

In a first aspect, the present invention provides a process for the preparation of a metal ion complex, the process comprising:
(a) contacting a metal in the form of particles having a bulk density of between about 0.2 and about 8.0 g/cm$^3$ with a chelating agent in solid form; and
(b) while the metal is in contact with the chelating agent, contacting the metal and chelating agent with an oxidising agent, to form at least one metal ion complex.

The process typically comprises the further step (c) of allowing the combination of agents resulting from step (b) to react until completion, i.e. allowing the oxidizing agent, metal and chelating agent to react until completion.

The inventors have surprisingly found that metal ion complexes having different properties to metal ion complexes prepared by prior art processes can be prepared using the process of the present invention and allowing the reaction to proceed until completion.

For example, processes described in the Examples of AU 2004205086 A1 afford the metal ion chelate complex Cu[EDTA]$^{2-}$. When copper and EDTA are used in the process of the present invention, and the reaction allowed to proceed to completion, a copper ion complex having different properties to Cu[EDTA]$^{2-}$ can be prepared.

In an embodiment, the bulk density of the metal is between about 0.3 and about 4.0 g/cm$^3$. In an embodiment, the bulk density of the metal is between about 0.8 and about 2.5 g/cm$^3$.

In an embodiment, the metal and chelating agent are above ambient temperature when the metal and chelating agent are contacted with the oxidising agent.

In an embodiment, the oxidising agent is above ambient temperature when the metal and chelating agent are contacted with the oxidising agent.

In an embodiment, the ratio of metal:chelating agent in moles is within the range of about 1:1 to 50:1.

In an embodiment, the ratio of chelating agent:oxidising agent in moles is within the range of about 1:1 to 1:20.

In an embodiment, the metal is selected from the group consisting of Cu, Zn, Mn, Fe, Co, Ni, Cr, A, Cd, Ag, Au, Se, and mixtures thereof.

In an embodiment, the metal is Cu.

In an embodiment, the chelating agent comprises a nitrogen and/or an oxygen donor.

In an embodiment, the chelating agent is selected from the group consisting of ethylenediaminetetraacetic acid (EDTA), diethylenetriaminepentaacetic acid (DTPA), hydroxyethylenediaminetetraacetic acid (HEDTA), ethylenediaminedisuccinic acid (EDDS), salicylic acid, acetyl salicylic acid, amine acids, peptides, and salts and hydrates thereof. In an embodiment, the amino acid is selected from the group consisting of glycine, histidine, lysine, arginine, cysteine, methionine and salts thereof, or mixtures thereof.

In an embodiment, the chelating agent is ethylenediaminetetraacetic acid (EDTA) or a salt thereof.

In an embodiment, the chelating agent is ethylenediaminetetraacetic acid (EDTA) disodium salt.

In an embodiment, the oxidising agent is selected from the group consisting of peroxides, peracids, ozone and oxidising salts.

In an embodiment, the oxidising agent is in solution when the metal and chelating agent are contacted with the oxidising agent.

In an embodiment, the oxidising agent is in aqueous solution when the metal and chelating agent are contacted with the oxidising agent.

In an embodiment, the peroxide is hydrogen peroxide.

In an embodiment, the hydrogen peroxide is in an aqueous solution.

In an embodiment, the aqueous solution of hydrogen peroxide has a concentration in the range of about 5 wt. % to about 6 wt. %.

In an embodiment, the aqueous solution of hydrogen peroxide has a concentration of about 50 wt. %.

In an embodiment, the metal is Cu, the chelating agent is ethylenediaminetetraacetic acid (EDTA) disodium salt and the oxidising agent is hydrogen peroxide.

In an embodiment, hydrogen peroxide is in an aqueous solution, the ratio of Cu:ethylenediaminetetraacetic acid (EDTA) disodium salt in moles is about 1:1 to about 50:1 and the ratio of Cu:hydrogen peroxide in moles is about 1:1 to about 1:20.

In an embodiment, Cu in contact with ethylenediaminetetraacetic acid (EDTA) disodium salt is maintained at above about 75° C. e.g. about 80° C. to 90° C.) when the Cu and EDTA are contacted with hydrogen peroxide, the hydrogen peroxide also being at above about 75° C. (e.g. about 80° C. to 90° C.).

In an embodiment, the process further comprises a step of removing unreacted metal and/or unreacted chelating agent and/or unreacted oxidising agent.

In a second aspect, the present invention provides a metal ion complex obtained by the process according to the first aspect.

In a third aspect, the present invention provides a composition comprising a metal ion complex or a mixture of metal ion complexes obtained by the process according to the first aspect.

In a fourth aspect, the present invention provides a formulation for topical administration comprising a metal ion complex or a mixture of metal ion complexes obtained by the process according to the first aspect.

In a fifth aspect, the present invention provides the use of a metal ion complex or a mixture of metal ion complexes obtained by the process according to the first aspect in the manufacture of a medicament for reducing inflammation, treating or preventing inflammation associated with arthritis, promoting hair growth, treating or preventing psoriasis, increasing blood flow, treating or preventing chilblains, treating or preventing varicose veins, treating a wound, promoting wound healing, treating or promoting healing of scar tissue, treating burns, alleviating or reducing joint pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease (MND; MND includes, for example, amyotrophic lateral sclerosis (ALS; also known as Lou Gehrig's Disease), primary lateral sclerosis (PLS), progressive muscular atrophy (PMA), progressive bulbar palsy (PBP) and pseudobulbar palsy), treating or preventing viral conditions, treating or preventing prion diseases (e.g. bovine spongiform encephalopathy (BSE), scrapie, Creutzfeldt-Jakob disease (CJD) or its variant (vCJD), Gerstmann-Sträussler-Scheinker syndrome, fatal familial insomnia or kuru), treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases (e.g. multiple sclerosis, Parkinson's disease, Alzheimer's disease, dementia, transverse myelitis or epilepsy), treating or preventing asthma or other bronchial and/or respiratory conditions, treating or preventing osteoporosis, bone fractures or other bone conditions, treating or preventing eye cataracts or other eye conditions, or combinations thereof.

In a sixth aspect, the present invention provides a method for reducing inflammation, treating or preventing inflammation associated with arthritis, promoting hair growth, treating or preventing psoriasis, increasing blood flow, treating or preventing chilblains, treating or preventing varicose veins, treating a wound, promoting wound healing, treating or promoting healing of scar tissue, treating burns, alleviating or reducing join: pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease (MND; MND includes, for example, amyotrophic lateral sclerosis (ALS; also known as Lou Gehrig's Disease), primary lateral sclerosis (PLS), progressive muscular atrophy (PMA), progressive bulbar palsy (PBP) and pseudobulbar palsy), treating or preventing viral conditions, treating or preventing prion diseases (e.g. bovine spongiform encephalopathy (BSE), scrapie, Creutzfeldt-Jakob disease (CJD) or its variant (vCJD), Gerstmann-Sträussler-Scheinker syndrome, fatal familial insomnia or kuru), treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases (e.g. multiple sclerosis, Parkinson's disease, Alzheimer's disease, dementia, transverse myelitis or epilepsy), treating or preventing asthma or other bronchial and/or respiratory conditions, treating or preventing osteoporosis, bone fractures or other bone conditions, treating or preventing eye cataracts or other eye conditions, or combinations thereof, in a human or animal, comprising administering to the human or animal a therapeutically effective amount of a metal ion complex or a mixture of metal ion complexes obtained by the process according to the first aspect.

In a seventh aspect, the present invention provides a metal ion complex comprising a ligand of Formula (I) or Formula (II)

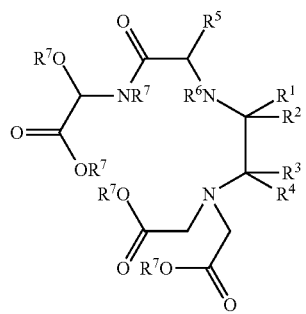

Formula (I)

-continued

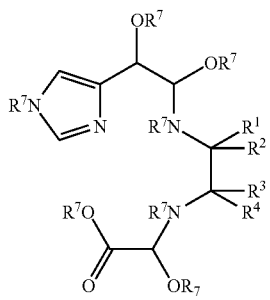

Formula (II)

wherein $R^1$ is H and $R^2$ is H or OH, or $R^1$ and $R^3$ together with the carbon atom to which they are attached form a carbonyl (C=O);

$R^3$ is H and $R^4$ is H or OH, or $R^3$ and $R^4$ together with the carbon atom to which they are attached form a carbonyl (C=O);

$R^5$ is —CHO($R^7$)$CH_2OR^7$, or —$CH_2CO_2R^7$ and $R^6$ is absent or H, or $R^5$ is H and $R^6$ is —CH(O$R^7$)$CE_2OR^3$ or —$CH_2CO_2R^7$; and each $R^7$ is independently absent or H;

or a salt thereof, tautomer thereof or polymer thereof.

In an embodiment, the ligand is of Formula (I) or a salt thereof, tautomer thereof or polymer thereof.

In an embodiment, $R^5$ is —CH(O$R^7$)$CH_2OR^7$ or —$CH_2CO_2R^7$ and $R^6$ is absent or H, or a salt thereof, tautomer thereof or polymer thereof.

In an embodiment, the ligand is of Formula (Ia)

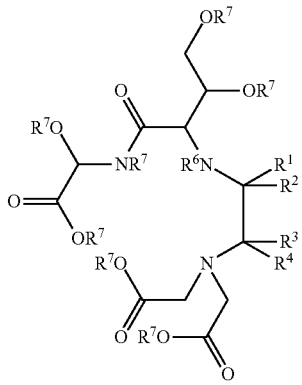

Formula (Ia)

wherein $R^1$ is H and $R^2$ is OH, or $R^1$ and $R^2$ together with the carbon atom to which they are attached form a carbonyl (C=O);

$R^3$ is H and $R^4$ is OH, or $R^3$ and $R^4$ together with the carbon atom to which they are attached form a carbonyl (C=O);

$R^6$ is absent: or H; and each $R^7$ is independently absent or H;

or a salt thereof, tautomer thereof or polymer thereof.

In an embodiment, the ligand is of Formula (Ib)

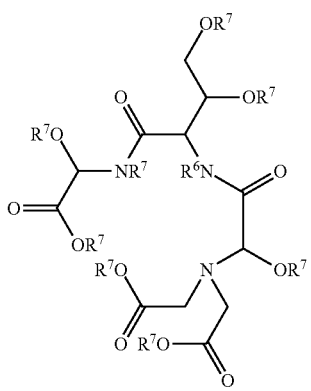

Formula (Ib)

wherein $R^6$ is absent or H; and each $R^7$ is independently absent or H;

or a salt thereof, tautomer thereof or polymer thereof.

In an embodiment, the ligand is of Formula (II) or a salt thereof, tautomer thereof or polymer thereof.

In an embodiment, the ligand is of Formula (IIa)

Formula (IIa)

wherein each $R^7$ is independently absent or H;

or a salt thereof, tautomer thereof or polymer thereof.

In an eighth aspect, the present invention provides a metal ion complex comprising:
  a metal ion; and
  a ligand;
wherein
the complex is a complex obtainable from the reaction of EDTA and $H_2O_2$ in the presence of copper and having an $^1H$ NMR in $D_2O$ substantially as depicted in FIG. 1, FIG. 2 or FIG. 3.

In an embodiment of the seventh or eighth aspect of the present invention, the metal ion complex comprises $Cu^{2+}$, $Cu^{3+}$ or a mixture of $Cu^{2+}$, and $Cu^{3+}$.

In a ninth aspect, the present invention provides a composition comprising a metal ion complex or a mixture of metal ion complexes according to the seventh or eighth aspect of the present invention, or a salt thereof, tautomer thereof or polymer thereof.

In a tenth aspect, the present invention provides a formulation for topical administration comprising a metal ion complex or a mixture of metal ion complexes according to the seventh or eighth aspect of the present invention, or a salt thereof, tautomer thereof or polymer thereof.

In an eleventh aspect, the present invention provides the use of a metal ion complex or a mixture of metal ion complexes according to the seventh or eighth aspects of the present invention, or a salt thereof, tautomer thereof or polymer thereof, in the manufacture of a medicament for reducing inflammation, treating or preventing inflammation associated with arthritis, promoting hair growth, treating or preventing psoriasis, increasing blood flow, treating or preventing chilblains, treating or preventing varicose veins, treating a wound, promoting wound healing, treating or promoting healing of scar tissue, treating burns, alleviating or reducing joint pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease (MND; MND includes, for example, amyotrophic lateral sclerosis (ALS; also known as Lou Gehrig's Disease), primary lateral sclerosis (PLS), progressive muscular atrophy (PMA), progressive bulbar palsy (PBP) and pseudobulbar palsy), treating or preventing viral conditions, treating or preventing prion diseases (e.g. bovine spongiform encephalopathy (BSE), scrapie, Creutzfeldt-Jakob disease (CJD) or its variant (vCJD), Gerstmann-Sträussler-Scheinker syndrome, fatal familial insomnia or kuru), treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases (e.g. multiple sclerosis, Parkinson's disease, Alzheimer's disease, dementia, transverse myelitis or epilepsy), treating or preventing asthma or other bronchial and/or respiratory conditions, treating or preventing osteoporosis, bone fractures or other bone conditions, treating or preventing eye cataracts or other eye conditions, or combinations thereof.

In a twelfth aspect, the present invention provides a method for reducing inflammation, treating or preventing inflammation associated with arthritis, promoting hair growth, treating or preventing psoriasis, increasing blood flow, treating or preventing chilblains, treating or preventing varicose veins, treating a wound, promoting wound healing, treating or promoting healing of scar tissue, treating burns, alleviating or reducing join: pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease (MND; MND includes, for example, amyotrophic lateral sclerosis (ALS; also known as Lou Gehrig's Disease), primary lateral sclerosis (PLS), progressive muscular atrophy (PMA), progressive bulbar palsy (PBP) and pseudobulbar palsy), treating or preventing viral conditions, treating or preventing prion diseases (e.g. bovine spongiform encephalopathy (BSE), scrapie, Creutzfeldt-Jakob disease (CJD) or its variant (vCJD), Gerstmann-Sträussler-Scheinker syndrome, fatal familial insomnia or kuru), treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases (e.g. multiple sclerosis, Parkinson's disease, Alzheimer's disease, dementia, transverse myelitis or epilepsy), treating or preventing asthma or other bronchial and/or respiratory conditions, treating or preventing osteoporosis, bone fractures or other bone conditions, treating or preventing eye cataracts or other eye conditions, or combinations thereof, in a human or animal, comprising administering to the human or animal a therapeutically effective amount of a metal ion complex or a mixture of metal ion complexes according to the seventh or eighth aspect of the present invention, or a salt thereof, tautomer thereof or polymer thereof.

In a further aspect, the present invention provides a metal ion complex or a mixture of metal ion complexes according to the seventh or eighth aspects of the present invention, or a salt thereof, tautomer thereof or polymer thereof, or a metal ion complex or a mixture of metal ion complexes obtained by the process according to the first aspect of the present invention, for use in reducing inflammation, treating or preventing inflammation associated with arthritis, promoting hair growth, treating or preventing psoriasis, increasing blood flow, treating or preventing chilblains, treating or preventing varicose veins, treating a wound, promoting wound healing, treating or promoting healing of scar tissue, treating burns, alleviating or reducing joint pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease (MND; MND includes, for example, amyotrophic lateral sclerosis (ALS; also known as Lou Gehrig's Disease), primary lateral sclerosis (PLS), progressive muscular atrophy (PMA), progressive bulbar palsy (PEP) and pseudobulbar palsy), treating or preventing viral conditions, treating or preventing prion diseases (e.g. bovine spongiform encephalopathy (BSE), scrapie, Creutzfeldt-Jakob disease (CJD) or its variant (vCJD), Gerstmann-Sträussler-Scheinker syndrome, fatal familial insomnia or kuru), treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases (e.g. multiple sclerosis, Parkinson's disease, Alzheimer's disease, dementia, transverse myelitis or epilepsy), treating or preventing asthma or other bronchial and/or respiratory conditions, treating or preventing osteoporosis, bone fractures or other bone conditions, treating or preventing eye cataracts or other eye conditions, or combinations thereof.

BRIEF DESCRIPTION OF THE FIGURES

Preferred embodiments of the present invention are described below, by way of example only, with reference to the accompanying drawings in which.

DETAILED DESCRIPTION OF EMBODIMENTS OF THE INVENTION

Figure 1:
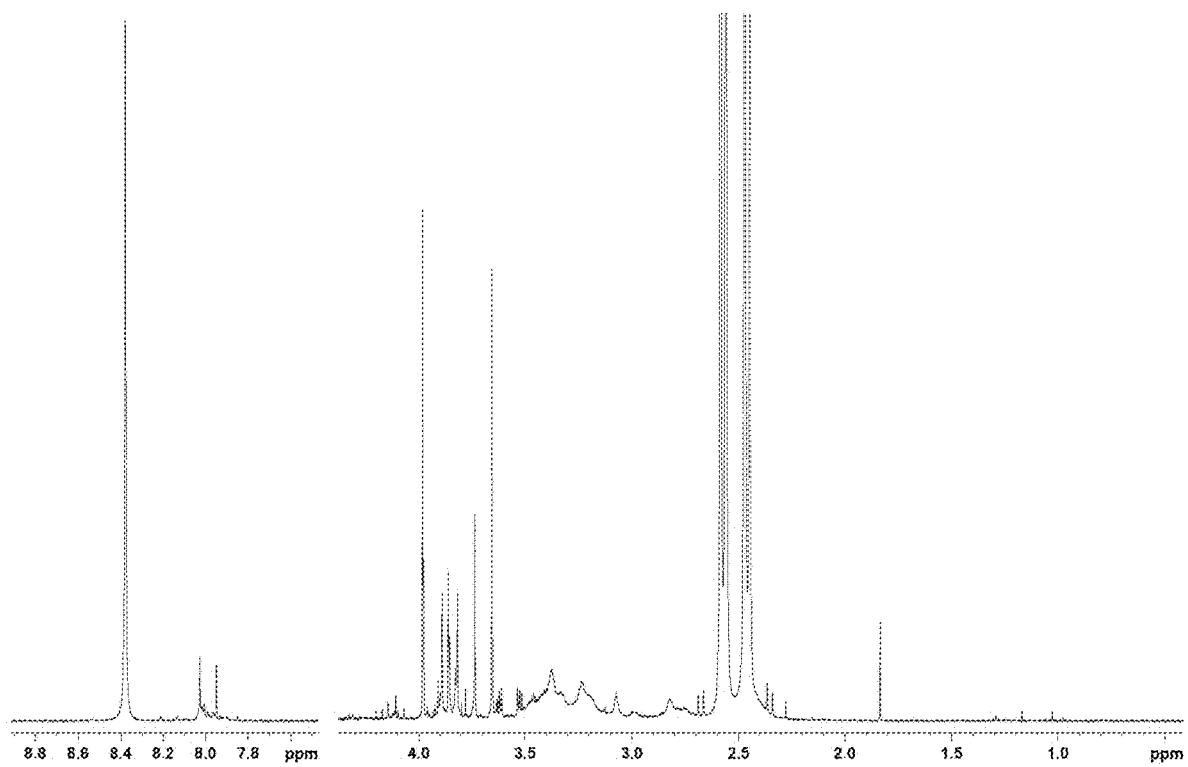
FIG. 1 is a 600 MHz $^1$H NMR spectrum of "Fraction 1" in $D_2O$ (as described in Example 19) plotted as signal intensity vs. chemical shift (ppm).

In a first aspect, the present invention provides a process for the preparation of a metal ion complex, the process comprising:
(a) contacting a metal in the form of particles having a bulk density of between about 0.2 and about 8.0 g/cm$^3$ with a chelating agent in solid form; and
(b) while the metal is in contact with the chelating agent, contacting the metal and chelating agent with an oxidising agent, to form at least one metal ion complex.

In the context of the present specification, the term "metal ion complex" should be understood to include metal ion complexes (whether charged or uncharged), as well as salts, protonated forms and hydrated forms thereof.

Whilst not seeking to be limited to any one proposed mechanism of formation, the process of forming the metal ion complex may involve an in situ redox reaction between the metal and the oxidising agent, whereby the metal is oxidised to one or more corresponding cations.

The metal cations thus produced may then chelate with the chelating agent to form the metal ion complex. Suitable combinations of oxidising agent and metal can be selected based on the reduction potential of the respective reagents. Reduction potentials are known to persons skilled in the art and are reported, for example, in the *CRC Handbook of Chemistry and Physics*, Weast, R., Ed. 55$^{th}$ Edition, 1974-1975.

By way of illustration, the following reaction may be envisaged, where the oxidising agent is hydrogen peroxide and M is a suitable metal:

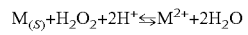

$$M_{(S)} + H_2O_2 + 2H^+ \leftrightarrows M^{2+} + 2H_2O$$

The resultant $M^{2+}$ ions are then able to form a metal ion complex with a ligand (e.g. a chelating agent).

The inventors have found that if metal in the form of particles having a bulk density of between about 0.2 and about 8.0 g/cm$^3$ is contacted with the chelating agent in solid form before the commencement of the oxidation reaction, and the reaction allowed to proceed to completion, metal ion complexes can be prepared that have different properties to metal ion complexes prepared when the chelating agent is in solution when the chelating agent is contacted with the metal.

Bulk density is a property of powders, granules, and other "divided" solids or particulate matter. It is the mass of the particles of the material divided by the total volume they occupy. The total volume includes particle volume, inter-particle void volume, and internal pore volume. The bulk density of the metal particles may be determined by, for example, adding 100 g of the metal particles to a 200 ml measuring cylinder (graduated cylinder). The initial volume measured in the measuring cylinder is the "freshly settled" volume. The measuring cylinder is then picked up and dropped 3 times from a height of 2 cm onto a solid surface. The volume measured in the measuring cylinder at this stage is the "tapped" volume. The bulk density is thus determined by the formula:

$$\text{bulk density (in g/mL or g/cm}^3\text{)} = \frac{100}{\text{measured volume (in mL or cm}^3\text{)}}$$

As used herein, all references to the bulk density of metal particles refer to the "tapped" bulk density, as determined by the procedure described above unless expressly stated otherwise. In the process of the present invention, a metal in the form of particles having a bulk density of between about 0.2 and about 8.0 g/cm$^3$ is used. In various embodiments, the metal has a bulk density of between about 0.3 and about 4.0 g/cm$^3$, for example, between about 0.5 and about 3.0 g/cm$^3$, between about 0.5 and about 2.5 g/cm$^3$, between about (0.7 and about 2.0 g/cm$^3$, between about 0.8 and about 1.7 g/cm$^3$ or between about 0.9 and about 1.5 g/cm$^3$.

In the process of the present invention, the metal may be any metal capable of forming a metal ion complex with the chelating agent. The metal used in the process is typically in its elemental state (i.e. an oxidation state of 0). The metal may, however, have an oxide (or other) layer on the metal in its elemental state. In an alternative embodiment, the metal is a metal salt which is oxidised to a higher oxidation state during the process to form the metal ion complex. For example, a Cu(I) salt (i.e. comprising $Cu^+$) may be oxidised to the Cu (II) salt (i.e. comprising $Cu^{2+}$) or to the Cu (III) salt (i.e. comprising $Cu^{3+}$), which then goes on to form the metal ion complex.

The metal is in the form of particles. The metal may, for example, be in the form of metal turnings, wire, ribbon, granules, powder, a solid bar having any shape, or any other suitable particulate form.

In some embodiments, the metal particles may have an oxide (or other) layer, or develop an oxide (or other) layer prior to being used in the process. In these embodiments, the term "contacting the metal" is taken to apply to contacting the bulk metal particles (i.e. the metal including any oxide (or other) layer) with the appropriate agent. This may occur by contacting the oxide (or other) layer exclusively, or contacting the oxide (or other) layer and the elemental metal simultaneously both the elemental metal and layer at the same time). The process of the invention embraces both of these alternatives, so long as the metal is able to react with the other agents. In some embodiments the metal may be pre-treated prior to the process in order to remove or reduce an oxide (or other) layer on the metal.

The chelating agent may be any compound capable of forming a metal ion complex with a cation of the metal. Metal ion complexes (also known as coordination complexes) formed by the process of the present invention comprise a metal cation having two or more coordinate bonds to the chelating agent. The chelating agent is thus a ligand having more than one site (e.g. functional group) capable of forming a coordination bond with a metal cation. The chelating agent may be described as being a multidentate (also known as polydentate) ligand.

Chelation between the metal and the chelating agent involves the formation or presence of two or more separate coordinate bonds between a multidentate (i.e. multiple bonded) ligand and a central atom (i.e. metal cation).

The chelating agent (i.e. multidentate ligand) may be charged or uncharged, so long as it is capable of forming a coordinate bond with a cation of the metal to form a metal ion complex. In some embodiments, the chelating agent (ligand) is an organic compound.

Chelating agents are also sometimes called chelants, chelators or sequestering agents.

In coordination chemistry, the bonding between a metal cation and a ligand generally involves formal donation of one or more of the ligand's electron pairs. The nature of metal-ligand bonding can range from covalent to ionic. Furthermore, the metal-ligand bond order can range from one to three. Ligands are sometimes viewed as Lewis bases, although rare cases are known to involve Lewis acidic ligands.

As used herein, the term "chelating agent" includes within its scope compounds capable of forming a multidentate ligand in situ under the conditions of the process of the present invention (i.e. a "chelating agent precursor"). In other words, the chelating agent contacted with the metal in the process of the present invention may be a compound that is not necessarily capable of acting as a multidentate ligand, but is transformed to a substance capable of acting as a multidentate ligand under the conditions experienced during the process of the invention.

The chelating agent is in solid form in step (a) of the process of the present invention. In this context, "solid form" refers to the chelating agent being a solid. Typically the chelating agent is in the form of a granulated or powdered solid. At least a portion of the chelating agent is in solid form when contacting the metal and when the metal and chelating agent is first contacted with the oxidising agent. Without wishing to be bound by theory, the inventors believe that the metal being in contact with the chelating agent in solid form when the metal and the chelating agent is contacted with the oxidising agent leads to a concentration gradient being established between the metal and the chelating agent in the resultant reaction mixture. Without wishing to be bound by theory, the inventors believe that, as a result of this concentration gradient, the process of the present invention can result in the formation of different metal ion complexes to those formed when the chelating agent is in solution prior to the chelating agent being contacted with the metal.

In an embodiment, the process of the invention forms a single species of metal ion complex. In other embodiments, the process of the invention forms multiple species of metal ion complexes (i.e. a mixture of metal ion complexes). These multiple species may be produced simultaneously at sequentially, and may be kept together as a mixture, or separated in a subsequent step.

The process of the present invention comprises contacting a metal with a chelating agent. In an embodiment, the metal is added to the chelating agent. In another embodiment, the chelating agent is added to the metal. In either of these embodiments, the end result is that the metal and chelating agent are in contact with each other. In other words, the metal and chelating agent are in intimate physical contact. In some embodiments, the metal and chelating agent are combined and mixed to form a mixture in which the metal and chelating agent are in contact with each other.

The process of the present invention comprises contacting the metal and chelating agent (while the metal is in contact with the chelating gent) with an oxidising agent. In an embodiment, the metal in contact with the chelating agent is added to the oxidising agent. In another embodiment, the oxidising agent is added to the metal and chelating agent (while the metal is in contact with the chelating agent).

In an embodiment, the oxidising agent is added to the metal/chelating agent at one time. In another embodiment, the metal/chelating agent is added to the oxidising agent at one time. Alternatively, in other embodiments, the oxidising agent is added to the metal/chelating agent in a portionwise fashion over a period of time. For example, the oxidising agent may be added portionwise over about 5 seconds to about 1 hour or 2 to 3 weeks. In other embodiments, the metal/chelating agent is added to the oxidising agent in a portionwise fashion over a period of time as above. In further alternative embodiments, the addition of the oxidising agent to the metal/chelating agent, or the metal/chelating agent to the oxidising agent, is performed in a continuous fashion over a period of time. For example, addition can be made by a syringe pump or solids addition funnel or other apparatus known to those skilled in the art. Those skilled in the art would be able to gauge an appropriate rate of addition taking into consideration factors such as concentration, temperature, reagents, etc.

In an embodiment, the process of the invention is carried out as a "one pot" process. In some embodiments, the process is carried out in a stepwise fashion, including stepwise addition of the oxidising agent and/or metal/chelating agent to the other.

In an embodiment, the metal/chelating agent is wetted with a solvent prior to contacting the oxidising agent. In some embodiments the metal/chelating agent is wetted with water prior to contacting the oxidising agent. In this regard, "wetted" refers to the application of an amount of solvent or water to the metal/chelating agent. This typically involves applying an amount sufficient to cover the metal/chelating agent.

The process of the present invention typically comprises the further step of allowing the combination of reagents resulting from the contact of the metal and chelating agent with the oxidising agent to react until completion. In other words, the oxidation reaction(s) initiated by the oxidising agent is(are) allowed to go to completion. Accordingly, in an embodiment, the present invention provides a process for the preparation of a metal ion complex, the process comprising:
  (a) contacting a metal in the form of particles having a bulk density of between about 0.2 and about 8.0 g/cm$^3$ (e.g. between about 0.3 and about 4.0 g/cm$^3$) with a chelating agent in solid form;
  (b) while the metal is in contact with the chelating agent, contacting the metal and chelating agent with an oxidising agent; and
  (c) allowing the resulting combination to react until completion.

In the context of the process of the present invention, there are several characteristics to indicate to a person skilled in the art that the reaction has gone to completion.

In an embodiment, the completion of the reaction may be indicated by an "exothermic explosion". The "exothermic explosion" may be considered a period towards the end of the reaction where the reaction enters an exothermic chase. For example, the exothermic reaction may lead to a thermal runaway or a runaway reaction whereby the heat generated from the exothermic nature of the reaction(s) increases the rate of the reaction in a positive feedback, leading to a period of highly exothermic reaction. In embodiments that contain solvents, particularly low-boiling solvents, or any other low-boiling reagent or component, these may be quickly converted to their gaseous states and have the appearance of an explosion. Other indicators that the reaction is reaching completion may include the release of water vapour, $CO_2$, ozone, oxygen and/or other gaseous products. In some embodiments, the reaction mixture appears to "boil" with bubbles of gaseous products. For example, and without wishing to be constrained by theory, in the case of an embodiment using Cu as the metal, disodium EDTA as the chelating agent and $H_2O_2$ as the oxidising agent, there is believed to be a decarboxylation event as the reaction nears completion, which affords bubbles of $CO_2$.

In other embodiments, the completion of the reaction may be indicated by a change in the colour of the reaction. In one embodiment that employs copper as the metal, the reaction mixture changes colour from blue to a greenish blue colour, indicating the completion of the reaction (e.g. from Pantone® 2386 C to Pantone® 306 UP).

In other embodiments, the completion of the reaction may be indicated by the formation of specific metal ion complexes as determined by chromatographic techniques, such as, for example, HPLC.

Allowing the combination to react until completion comprises allowing the combination to react for a sufficient period of time for the reaction to proceed until completion. In some embodiments, allowing the resulting combination to react until completion involves allowing the combination to react for extended periods, for example, the combination may be left for 2 to 5 weeks in order to go to completion. In some embodiments, the combination will react for 1 day, 2 to 7 days, 1 to 2 weeks or 1 to 3 weeks before entering an exothermic phase. In embodiments where the reaction mixture is heated at the outset, it is more likely that the reaction will go to completion within a shorter period of time. For example, the reaction may go to completion in about 5 to 15 mins, about 15 to 30 mins about 30 rains to 1 hour or about 1 to 2 hours, when the reaction components are heated.

In some embodiments, the combination will react until all of the oxidising agent is consumed. In other embodiments, the combination will react until all of the chelating agent is consumed. In other embodiments still, the combination will react until all of the metal is consumed. In some embodiments, the process further comprises a step of removing unreacted metal and/or unreacted chelating agent and/or unreacted oxidising agent.

In an embodiment, mixtures of different metals are used. In an embodiment, the metal used in the process is an alloy comprising two or more metals, with at least one metal being capable of forming a metal ion complex. In another embodiment, the alloy comprises two or more metals with more than one metal being capable of forming a metal ion complex.

In an embodiment, the metal and chelating agent are above ambient temperature (for example at above about 30° C., above about 40° C., above about 50° C., above about 60° C., above about 70° C., above about 75° C., above about 80° C. or at about 85° C.; e.g. In the range of about 30° C. to about 100° C., about 39° C. to about 90° C., about 30° C. to about 80° C., about 40° C. to about 90° C., about 60° C. to about 90° C. or about 80° C. to 90° C.: when the oxidising agent is contacted with the metal and chelating agent. In some embodiments, the metal and chelating agent are heated before the oxidising agent is contacted with the metal and chelating agent.

In an embodiment, the oxidising agent is above ambient temperature when it is contacted with the metal and chelating agent. In an embodiment the oxidising agent is hot when contacting the metal and chelating agent. For example, the oxidising agent may be at above about 30° C., above about 40 DC, above about 50° C., above about 60° C., above about 70° C., above about 75 CC, above about 80° C. or at about 85° C.; e.g. In the range of about 30° C. to about 100° C., about 30° C. to about 90° C., about 30° C. to about 80° C., about 40° C. to about 90° C., about 60° C. to about 90° C. or about 80° C. to 90° C.

In some embodiments, both the metal/chelating agent and the oxidising agent are above ambient temperature.

In some embodiments, both the metal/chelating agent and the oxidising agent are above ambient temperature when contacting each other.

In an embodiment, the metal and chelating agent are heated when the oxidising agent is contacted with the metal and chelating agent. In an embodiment, heat is applied to the metal before it contacts the chelating agent, thereby elevating the temperature of the metal/chelating agent above ambient temperature. In an alternative embodiment, heat is applied to the chelating agent before it contacts the metal, thereby elevating the temperature of the metal/chelating agent above ambient temperature. In another embodiment, heat is applied to the metal/chelating agent while the metal is in contact with the chelating agent, and before the oxidising agent is contacted with the metal and chelating agent, in order to bring it to above an ambient temperature. In another embodiment, heat is applied to the metal/chelating agent whilst the oxidising agent contacts the metal/chelating agent.

In an embodiment, heat is applied during step (b) to raise the temperature above ambient. In an embodiment, the hear is applied during step (c) to raise the temperature above ambient.

In some embodiments heat Is applied continuously, whilst in other embodiments the heat is applied at time intervals that may be regular or irregular. Heat may be applied, for example, by means of a heating mantle, heating jacket, hotplate, microwave or any other means, or any combination thereof, in order to raise the temperature above ambient temperature.

Modification of the temperature may be used to control the rate of reaction. Accordingly, the process may optionally include one or more heating or cooling steps at any stage. For example, heat may be applied to the reaction in order to encourage the reaction to go to completion in a shorter period of time.

In an embodiment, the ratio of metal:chelating agent in moles is within the range of about 1:5 to about 100:1. In various embodiments, the ratio of metal:chelating agent is within the range of about 1:1 to about 50:1, about 1:1 to about 40:1, about 1:1 to about 10:1, about 2:1 to about 30:1, about 3:1 to about 20:1, about 4:1 to about 20:1, or about 4:1 to about 10:1. In some embodiments the ratio is about 5:1. In some embodiments, an excess of metal is used.

In an embodiment, the ratio of chelating agent:oxidising agent in moles is within the range of about 2:1 to about 1:100. In various embodiments, the ratio of chelating agent: oxidising agent is within the range of about 1:1 to about 1:50, about 1:1 to about 1:20, about 1:2 to about 1:20, about 1:2 to about 1:10 or about 1:3 to about 1:5. In some embodiments the ratio is about 1:3.3.

In an embodiment, the metal ion complex prepared by the process of the invention is water soluble.

In an embodiment, the amount of metal added is sufficient to consume substantially all of the oxidising agent. In another embodiment, the amount of chelating agent added is sufficient to complex substantially all of the metal ions.

In some embodiments, adding an excess of the chelating agent may slow the reaction down.

In an embodiment, about 50 to about 500 grams of metal is used. In various other embodiments, about 130 to about 1000 grams, about 0.5 kg to about 5 kg, about 1 kg to about 10 kg, about 5 kg to about 50 kg, about 10 kg to about 100 kg, about 50 kg to about 250 kg of metal is used.

In one embodiment the resultant metal ion complex is a salt, such as an alkali earth or alkali metal salt. For example, the metal ion complex may be a $Na^+$, $K^+$, $Li^+$, $Mg^{2+}$, or $Ca^{2+}$ salt.

In an embodiment, the metal to be used in the process of the invention is a transition metal. In another embodiment the metal is an alkaline earth metal. In an embodiment the metal is selected from the group consisting of Cu, Mn, Fe, Co, Ni, Zn, Cr, Al, Cd, Ag and Se and mixtures thereof.

In one embodiment the metal is copper.

In one embodiment the metal is copper which is oxidised to $Cu^{3+}$, $Cu^{2+}$ or $Cu^-$ ions, or a mixture thereof. In another embodiment the metal is iron which is oxidised to $Fe^{2+}$ or $Fe^{3+}$ ions, or a mixture thereof.

In a further embodiment the metal is zinc which is oxidised to $Zn^{2+}$ ions. In another embodiment the metal is Ni which is oxidised to $Ni^{2+}$ ions. In a further embodiment the metal is cobalt which is oxidised to $Co^{2+}$ or $Co^{3+}$ ions, or a mixture thereof. In another embodiment the metal is silver which is oxidised to $Ag^+$ ions.

Without wishing to be bound by theory, it is believed that one factor in the observed biological activity of copper complexes prepared by the process of the present invention as described in Examples 20 to 22 may be due to the formation of relatively stable complexes of $Cu^{3+}$.

In an embodiment, the chelating agent is a multidentate ligand capable of forming a stable metal ion complex. In an embodiment, the chelating agent is bidentate. In an embodiment, the chelating agent is tridentate. In an embodiment, the chelating agent is tetradentate. In an embodiment, the chelating agent is pentadentate. In an embodiment, the chelating agent is hexadentate.

In an embodiment, the chelating agent is neutral. In an embodiment, the chelating agent is positively charged. In an embodiment, the chelating agent is negatively charged. In an embodiment, the chelating agent is zwitterionic. In an embodiment, the chelating agent is used as its corresponding hydrate. In embodiments that include charged chelating agents, the chelating agent may be used as any suitable salt (i.e. a charged chelating agent with any suitable counterion).

In an embodiment, the chelating agent comprises a nitrogen and/or an oxygen donor. In this regard, the nitrogen and/or oxygen atom is part of a functional group on the chelating agent. The nitrogen and/or oxygen atom is able to donate electrons to the metal centre to thus form a coordinate bond and thus the coordinate complex (i.e. metal ion complex). In some embodiments, the donor on the chelating agent is a nitrogen. In some embodiments, the donor on the chelating agent is an oxygen. In some embodiments, the chelating agent comprises both a nitrogen and an oxygen donor. In some of such embodiments, not all of the nitrogen and/or oxygen donors form a coordinate bond with the metal centre. In some embodiments, the chelating agent comprises a sulfur donor.

In an embodiment the chelating agent comprises at least one carboxylic acid (or carboxylate) group. In one embodiment the chelating agent comprises at least one amino group, wherein the amino group may be a primary, secondary or tertiary amino group. In one embodiment the chelating agent may comprise at least one, e.g. 1, 2, 3, 4, 5 or 6, iminodiacetic acid [—$N(CH_2CO_2H)_2$] groups, wherein one or both of the methylene (—$CH_2$) hydrogen atoms may be replaced with another substituent, such as a $C_1$-$C_4$ alkyl group.

In an embodiment, the chelating agent is selected from the group consisting of etlhylenediaminetettaacetic acid (EDTA), diethylenetriaminepentaacetic acid (DTPA), hydroxyethylenediaminetetraacetic acid (HEDTA), ethylenediardnedisucciric acid (EDDS), salicylic acid, acetyl salicylic acid, amino acids, peptides, and salts and hydrates thereof. The structures of EDTA, DTPA, HEDTA and EDDS are shown

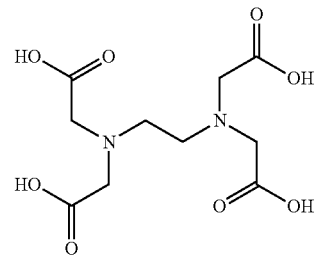

EDTA

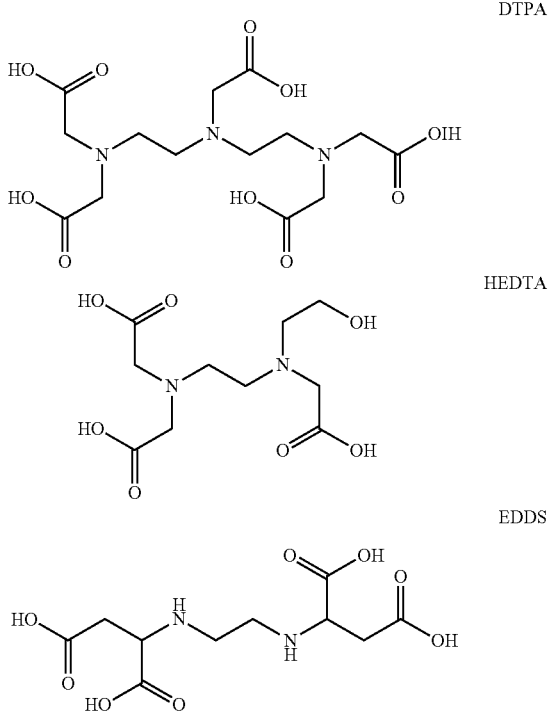

EDTA is a hexadentate chelating ligand with 6 possible coordination sites. The pKa of the carboxylic acid residues of EDTA are 1.70, 1.60, 6.30 and 10.60, respectively.

Neutral EDTA can exist as a zwitterion with one or two protons located on one or two of the nitrogen atoms.

EDTA, DTPA, and HEDTA have a strong affinity for a wide range of metal ions including $Cu^{3+}$, $Ag^+$, $Ca^{2+}$, $Co^{3+}$, $Fe^{3+}$, $Fe^{2+}$, $Mg^{2+}$, $Ni^{2+}$ and $Zn^{2+}$.

In one embodiment the chelating agent comprises amino acids such as glycine, histidine, lysine, arginine, cysteine, methionine, and peptides comprising those amines, and salts thereof. The peptide may comprise two, three, four or five amino acids. The respective amino acids may be the same or different. In one embodiment, the peptide is a dipeptide or a tripeptide.

In one embodiment the chelating agent is EDTA or a salt thereof. In an embodiment, the salt of EDTA comprises one or more of sodium ions, potassium ions, lithium ions, calcium ions, magnesium ions, or mixtures thereof. In one embodiment, the chelating agent is EDTA disodium salt. In another embodiment the chelating agent is DTPA or a salt thereof, or a sodium salt thereof.

At least a portion of the chelating agent is in solid form when the metal and chelating agent are first contacted with the oxidising agent in step (b). In an embodiment, at least a portion of the chelating agent remains in solid form during step (c).

In an embodiment, the oxidising agent is selected from the group consisting of peroxides, peracids, ozone and oxidising salts. In an embodiment, the oxidising agent is an N-oxide such as TEMPO.

In an embodiment, the oxidising agent is in solution when contacting the metal and chelating agent. The solvent used to make the solution may be any suitable solvent. In order to be suitable, the oxidising agent should not react with (or react to any appreciable amount with) the solvent. In addition, the oxidising agent should maintain its ability to act as an oxidising agent while in solution. In an embodiment, the oxidising agent is in an aqueous solution. In an embodiment, the aqueous solution comprises a cosolvent.

In an embodiment, the oxidising agent is hydrogen peroxide. In an embodiment, the hydrogen peroxide is in an aqueous solution.

In an embodiment, the aqueous solution of hydrogen peroxide comprises hydrogen peroxide in an amount within the range of about 0.01 wt. to about 100 wt. %. For example, in various embodiments, the aqueous solution of hydrogen peroxide is within the range of about 0.01 wt. % to about 70 wt. %, about 0.5 wt. % to about 60 wt. %, about 1 wt. % to about 60 wt. %, about 1 wt. % to about 15 wt. %, about 15 wt. % to about 30 wt. %, about 20 wt. % to about 30 wt. about 30 wt. % to about 40 wt. %, or about 45 wt. % to about 55 wt. %. In an embodiment, the aqueous solution of hydrogen peroxide is about 50 wt. %.

In an embodiment, the metal is Cu, the chelating agent is ethylenediaminetetraacetic acid (EDTA) disodium salt and the oxidising agent is hydrogen peroxide. In a further embodiment, the hydrogen peroxide is in an aqueous solution, the ratio of Cu:ethylenediaminetetraacetic acid (EDTA) disodium salt in moles is about 1:1 to about 50:1 and the ratio of Cu:hydrogen peroxide in moles is about 1:1 to about 1:20.

In another embodiment, Cu in contact with ethylenediaminetetraacetic acid (EDTA) disodium salt is maintained at above about 75° C. when the Cu and EDTA are contacted with the hydrogen peroxide, the hydrogen peroxide also being at above about 75° C. In this embodiment, the Cu and EDTA disodium salt may be mixed by any suitable mixing techniques known to those skilled in the art. For example, mixing may be performed by mechanical or magnetic stirring, sonication, shaking, swirling, folding, whipping, inverting the reaction vessel etc.

In an embodiment, the process further comprises a stop of removing unreacted metal and/or unreacted chelating agent and/or unreacted oxidising agent.

Metal ion complexes prepared according to the present invention may be more stable at a particular pH. For example, metal ion complexes according to the present invention may be stable at a pH in the range from about 4 to about 12, preferably in the range from about 4 to about 9. Accordingly, the metal ion complex may be combined with a buffer or a pH adjusting agent to provide a stable composition comprising the metal ion complex.

In some embodiments, the metal ion complex comprises the chelate (i.e. ligand) and metal ion in a 1:1 stoichiometric ratio or 1:2 stoichiometric ratio (i.e. 1:1 or 1:2 chelate:metal ion). In other embodiments, the metal ion complex comprises the chelate and metal ion in a chelate:metal ion stoichiometric ratio of between 1:3 and 1:8, for example 1:3, 1:4, 1:5, 1:6, 1:7 or 1:6. Suitable counterions may include pharmaceutically acceptable ions such as sodium ions, potassium ions, calcium ions, magnesium ions, etc.

In some embodiments, the metal ion complex comprises multiple metal cations (i.e. one or more ligands are coordinated to two or more metal cations). In some embodiments, oligomers of metal ion complexes are formed.

In some embodiments, the process comprises an additional ion exchange step in order to exchange counterions. Techniques for performing such a step, such as ion exchange chromatography and recrystallization, are known to those skilled in the art. Thus, for example, a salt or protonated form of a metal ion complex (or mixture thereof) may be converted into another salt of choice.

The process according to the Invention may further include an additional step of isolating the metal ion complex from solution. Suitable methods of isolation include solvent evaporation, recrystallisation, solvent extraction, and other general methods known to those skilled in the art. In one embodiment, the mixture resulting from the process is evaporated or lyophilized to obtain a solid comprising the metal ion complex. The metal ion complex may be purified, e.g. by chromatographic techniques or by recrystallization from a suitable solvent.

The inventors have found that novel metal ion complexes comprising a ligand of Formula (I) or Formula (II) as defined below can be formed by the process according to the first aspect of the present invention.

Accordingly, in an aspect, the present invention provides a metal ion complex comprising a ligand of Formula (I) or Formula (II)

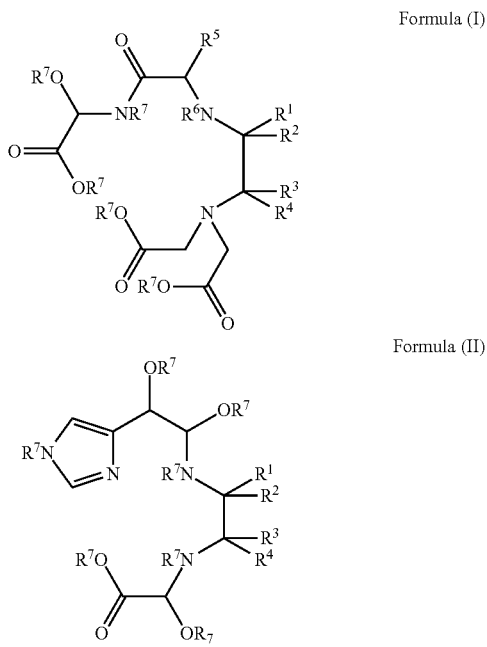

Formula (I)

Formula (II)

wherein
$R^1$ is H and $R^2$ is H or OH, or $R^1$ and $R^2$ together with the carbon atom to which they are attached form a carbonyl (C=O);
$R^3$ is H and $R^4$ is H or OH, or $R^3$ and $R^4$ together with the carbon atom to which they are attached form a carbonyl (C=O);
$R^5$ is —CH(OR$^7$)CH$_2$OR$^7$ or —CH$_2$CO$_2$R$^7$ and $R^6$ is absent or H, or $R^5$ is H and $R^6$ is —CH(OR$^7$) CH$_2$OR$^7$ or —CH$_2$CO$_2$R$^7$; and
each $R^7$ is independently absent or H;
or a salt thereof, tautomer thereof or polymer thereof.

Such metal ion complexes can be prepared by the process according to the present invention. For example, the inventors have found that when the process of the present invention is carried out using the metal copper, the chelating agent EDTA and the oxidising agent hydrogen peroxide, and the reaction is allowed to proceed to completion, the metal ion complexes prepared by the process include copper ion complexes comprising the ligand of Formula (III) or Formula (IV) described below (where M in Formula (III) or Formula (IV) is $Cu^{2+}$ or $Cu^{3+}$). Metal ion complexes comprising a ligand of Formula (I) or Formula (II) can also be formed by other methods. For example, the ligand may be synthesised by methods known in the art, and reacted with (or coordinated to) a metal for metal cation) to form the metal ion complex.

In the ligands of Formula (I) and Formula (II), the substituents $R^6$ and $R^7$ may, in some instances, represent H or may be absent. As a person skilled in the art will appreciate, if $R^6$ or $R^7$ are absent, the valency of the heteroatom to which the $R^6$ or $R^7$ is attached (i.e. the N and/or O atom) will be assumed to be satisfied by a lone pair of electrons (resulting in a formal negative charge on the heteroatom). In such instances, the lone pair of electrons/negative charge may, for example, form a salt with another cation (such as $Na^+$, $K^+$, $Ca^{3+}$ etc.) or may, for example, coordinate (i.e. bond) with a metal cation to form a coordination bond (sometimes known as a dative bond) and thus contribute to forming the coordination complex (i.e. metal ion complex). In other words, the negative charge of the —O$^-$, —N$^-$— or —CO$_2^-$ group (provided by the lone pair of electrons) is available for bonding with a proton (H'), cation (such as $Na^+$, $K^+$, $Ca^{2+}$ etc.) or the metal ion of the metal Lon complex.

For example, in the ligands of Formula (I) or Formula (II, —CO$_2$R$^7$ may represent —CO$_2$H (i.e. a carboxylic acid) when R is H, or —CO$_2^-$ (i.e. a carboxylate anion) when $R^7$ is absent. Depending on the conditions (pH for example), a carboxylic acid (i.e. —CO$_2$H) may deprotonate to afford the corresponding carboxylate anion (i.e. —CO$_2^-$). Also depending on the conditions, the carboxylate anion may form a salt, for example —CO$_2$Na (sometimes depicted as —CO$_2^-$Na$^+$), or may coordinate with the metal ion of the metal ion complex, forming a coordinate bond. This may be depicted, for example, as —CO$_2$ML$_n$, where M represents the metal ion of the metal ion complex and L$_n$ represents n ligands or ligating groups where n is an integer. Examples of ligating groups may include functional groups (such as —O$^-$, —OH, —N$^-$—, —NH—, —CO$_2$H, —CO$_2^-$—, etc.) on a ligand.

The nature of the coordinate bond, in terms of covalent or ionic character, between a ligand and a metal ion will depend on a number of factors. As a person skilled in the art will appreciate, a bond between a ligand and a metal ion may be ionic, covalent or somewhere in between. The degree of the partial ionic character for partial covalent character) of a bond may depend on, for example, the electronegativity of the metal ion and/or the electronegativity of the ligating group involved. For example, when the difference in electronegativity between the metal ion and the ligating group is greater, the bond will have a more ionic character. Similarly, when the difference in electronegativity between the metal ion and the ligating group is smaller, the bond will have a more covalent character. The metal ion complexes of the seventh aspect of the present invention comprise a ligand of Formula (I) or Formula (IT), as described above, bound to a metal ion by 2 or more bonds that may be ionic, covalent, partially ionic, partially covalent or may have any degree of partial ionic character or partial covalent character.

The metal ion complexes of the seventh aspect of the present invention may form tautomers (i.e. may exist in multiple tautomeric forms). A person skilled in the art will understand that tautomers are structural isomers that exist as a rapidly-interconverting mixture in equilibrium. The ratio of the tautomers depends on various factors, for example, temperature, solvent and pH. Most commonly, tautomers differ by the position of a proton. In other words, a deprotonation/protonation sequence occurs to relocate a proton.

When the ligands of Formula (I) or Formula (II) have a tautomer, each tautomer is embraced in the relevant Formula. For example, Formula (I) embraces both tautomers depicted in the below partial structures:

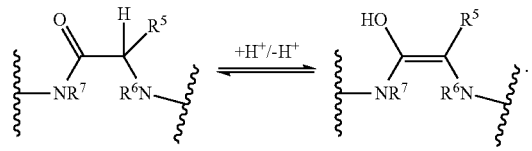

As a further example of tautomeric forms, Formula (I) embraces both tautomers depicted in the below partial structures:

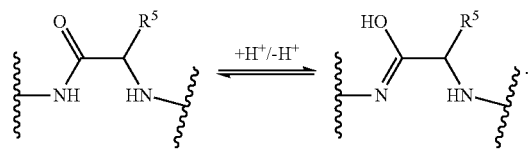

The ligands of Formula (Z) or Formula (II) may exist in stereoisomeric forms (e.g. enantiomers or diastereomers depending or the number of chiral centers). Mixtures of diastereomers and mixtures of enantiomers (e.g racemates) can be separated into the stereoisomerically uniform constituents by methods known to persons skilled in the art. Unless otherwise stated, it is intended that any reference herein to a compound or ligand that is capable of existing in stereoisomeric forms (e.g. a metal ion complex comprising a ligand of Formula (I) or Formula (II)) is intended to encompass all possible stereoisomers and mixtures of stereoisomers of the compound or ligand (e.g. is intended to encompass all possible enantiomers, mixtures of enantiomers, diastereomers or mixtures of diastereomers).

In some embodiments, the metal ion complex comprising a ligand of Formula (I) or Formula (II) comprises a metal ion selected from an ion of Cu, Zn, Mn, Fe, Cu, Ni, Cr, Al, Cd, Ag, Au and Se (e.g. $Cu^{2+}$, $Cu^{3+}$, $Zn^{2+}$, $Fe^{2+}$, $Fe^{3+}$, $Co^{2+}$, $Co^{3+}$, $Ni^{2+}$ or $Ag^+$).

A metal ion complex comprising a ligand of Formula (I) or Formula (II) may form a polymer. As used herein, the terms "polymer" and "polymers" are used in the broadest sense and include an oligomer, oligomers, oligomeric material and the like, unless the context clearly requires otherwise. That is, the terms "polymer" and "polymers" as used herein are intended to include dimers, trimers, tetramers etc. (i.e. comprising 2, 3, 4 etc. monomeric/repeating units or entities). For example, the term "polymer" may be used herein to refer to 2, 3, 4, 20, 50, 100, 1000, 10000, 100000 etc. monomeric/repeating units or entities.

In an embodiment, a polymer of the metal ion complex comprising a ligand of Formula (I) or Formula (II) may be provided by the polymerisation of a ligand of Formula (I) and/or Formula (II). A person skilled in the art will understand that the ligands of Formula (I) and Formula (II each have functional groups capable of forming covalent bonds (e.g. esters, amides, ethers etc.). Accordingly, polymers may, in various embodiments, be formed by the polymerisation of the functional groups of the ligands of Formula (I) and/or Formula (II) leading to polyesters, polyamides, polyethers etc. For example, a carboxylic acid group residing on the ligand of Formula (I) may form an ester with an alcohol group (—OH) on either a ligand of Formula (I) or Formula (II) to form an ester bond.

In another embodiment, the polymer of the metal ion complex comprising a ligand of Formula (I) or Formula (II) is a coordination polymer. A coordination polymer may be described as a structure containing metal cations linked by organic ligands. A coordination polymer may also be described as a coordination compound with repeating coordination entities extending in 1, 2 or 3 dimensions, or as a polymer whose monomeric/repeat units are coordination complexes. Coordination polymers may extend along a single dimension (and may include cross-links between two or more individual chains), or may extend in 2 or 3 dimensions. In some embodiments, the coordination polymer comprises a metal cation bound to more than 1 (e.g. 2, 3, 4, 5 or 6) ligands of Formula (I) and/or Formula (II). In other embodiments, the coordination polymer comprises ligand of Formula (I) and/or Formula (II) bound to more than 1 (e.g. 2, 3, 4, 5 or 6) metal cations.

Polymers of metal complexes comprising a ligand of Formula (I) and/or Formula (II) may form during the formation of the complex, or may form during the formation of the ligands. In other words, the metal complexes may polymerise during their formation, or the ligands may be polymerised prior to formation of the metal ion complex.

Polymers may be formed solely from metal ion complexes comprising a ligand of Formula (I), or may be formed solely from metal ion complexes comprising a ligand of Formula (II) (i.e. homopolymers). Alternatively, polymers may also be formed from a mixture of metal ion complexes comprising a ligand of Formula (I) and metal ion complexes comprising a ligand of Formula (II) (i.e. copolymers). The copolymers may, for example, be random copolymers, alternating copolymers or block copolymers.

The polymers may, for example, comprise between 2 and 20000 monomeric/repeating units/entities, for example, between about 2 and about 15000 monomeric units, between about 5 and about 10000 monomeric units, between about 10 and about 5090 monomeric units, between about 20 and about 2000 monomeric units, between about 100 and 1000 monomeric units or between about 500 and 5000 monomeric units.

The metal ion complexes of the eighth aspect of the present invention may also form polymers, as discussed above.

In the metal ion complexes of the seventh aspect of the present invention, the ligand may be coordinated to the metal ion of the metal ion complex by between 2 and 6 ligating groups (e.g. donor atoms). For example, the ligand may be coordinated to the metal ion of the metal ion complex by between 2 and 4 ligating groups (e.g. donor atoms) or by between 4 and 6 ligating groups (e.g. donor atoms). For example, the ligand may be attached to the metal ion of the metal ion complex by 2, 3, 4, 5 or 6 bonds between the metal ion and the ligand of Formula (I) or Formula (II). In other words, bonds occur between 2, 3, 4, 5 or 6 ligating groups (e.g. donor atoms) of the ligand and the metal ion of the metal ion complex. In an embodiment, the metal ion complex comprises a ligand of Formula (I) or Formula (II) and a metal ion, wherein the ligand is coordinated to the metal ion by 4 coordinate bonds. In another embodiment, the metal ion complex comprises a ligand of Formula (I) or Formula (II) and a metal ion, wherein the ligand is coordinated to the metal ion by 6 coordinate bonds.

It is likely that the ligating groups of the ligands of Formula (I) or Formula (II) are the donor atoms N and/or O.

These donor atoms may be present in various functional groups and may be in their charged or uncharged states. For example, the metal ion may bond to the donor atoms N and/or O, which are present in the ligands of Formula (I) or Formula (II) in the functional groups —OH, —O⁻, —NH—, —N⁻—, CO₂H, CO₂⁻, =N— or =O.

For example, in some embodiments, the metal ion complex may comprise a ligand attached to a metal ion by 4 bonds, as represented by Formula (III) or Formula (IV) as depicted below (where M is a metal ion):

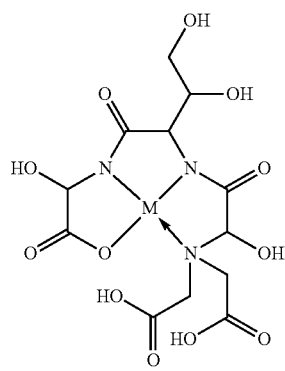

Formula (III)

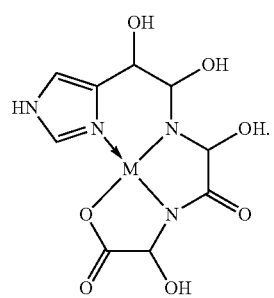

Formula (IV)

As a person skilled in the art will appreciate, the structures depicted in Formula (III) and Formula (IV) are a generalisation only, as various protonation/deprotonation steps will occur to give rise to tautomers of the structures of Formulas (III) and (IV). For example, the imidazole of Formula (IV) may deprotonate and tautomerise to give a structure of Formula (IVa):

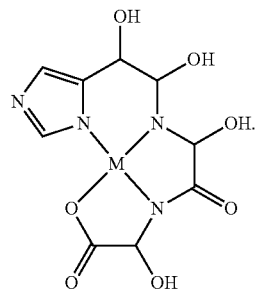

Formula (IVa)

As a person skilled in the art will also appreciate, the ligands may also bind to the metal ion by further coordination bonds. For example, one of the pendant carboxylic acid groups of Formula (III) may also bind to the metal centre to give the structure depicted in Formula (IIIa) below:

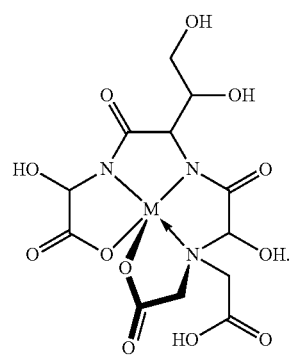

Formula (IIIa)

Further coordination may afford the structure depicted in Formula (IIIb):

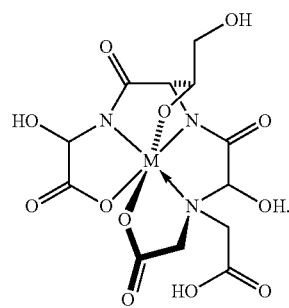

Formula (IIIb)

Without wishing to be bound by theory, it may also be possible for a ligand to coordinate to the metal ion via a contiguous series of 2 or more atoms (i.e. have a hapticity of 2 or more). For example, it may be possible for the ligand of Formula (II) to bind to the metal via the 5 contiguous atoms of the imidazolate group (i.e. hapticity of 5, $\eta^5$), as depicted below in Formula (V).

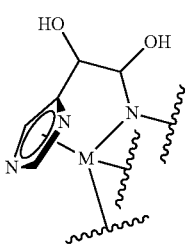

Formula (V)

Accordingly, in some embodiments, the metal ion complex comprises a a ligand coordinated to the metal ion via a contiguous series of 2 or more atoms (i.e. having a hapticity of 2 or more), for example, having a hapticity of 2 ($\eta^2$), 3 ($\eta^5$), 4 ($\eta^4$) or 5 ($\eta^5$).

The metal ion complexes described herein may form salts. Although the salts are preferably pharmaceutically acceptable, as discussed below, it will be appreciated that non-pharmaceutically acceptable salts of the metal ion complexes also fall within the scope of the present invention. Non-pharmaceutically acceptable salts may be useful as intermediates in the preparation of pharmaceutically acceptable salts (for example, by ion exchange such as ion exchange chromatography and/or precipitation, flocculation etc.).

For therapeutic applications of the metal ion complexes, the salts are preferably pharmaceutically acceptable, that is, a salt which is not deleterious to a subject to whom the salt is administered. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic an: hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Pharmaceutically acceptable salts may also be formed with amino acids having positively charged side-chains (e.g. arginine, histidine and lysine), negatively charged side-chains (e.g. aspartic acid and glutamic acid), polar uncharged side-chains (e.g. serine, threonine, asparagine and glutamine), hydrophobic side-chains (e.g. alanine, valine, isoleucine, methionine, phenylalanine, tyrosine and tryptophan) or other side-chains (e.g. cysteine, selenocysteine, glycine and proline).

The metal ion complexes obtained by the process of the first aspect of present invention and the metal ion complexes of the seventh and eighth aspects of the present invention (including salts thereof, tautomers thereof and polymers thereof) may, in certain circumstances or conditions, aggregate to form a supramolecular assembly. Accordingly, in some embodiments, the present invention provides a supramolecular assembly comprising two or more metal ion complexes of the seventh or eighth aspects of the present invention or obtained by the process of the first aspect of present invention. Supramolecular assemblies comprising the metal ion complexes of the present invention may be loosely held together (e.g. by Van der Waals, dispersion or electrostatic forces) and disassemble under certain conditions.

In addition, some of the metal ion complexes of the present invention may form solvates with water or common organic solvents. Such solvates are encompassed within the scope of the invention.

Pharmaceutical Compositions

The inventors have found that metal ion complexes obtained by the process of the first aspect of present invention (including salts thereof, tautomers thereof and polymers thereof) may have therapeutic activity. For example, the complex obtained by the process of the first aspect of the present invention using Cu, EDTA and hydrogen peroxide and allowing the reaction to proceed to completion, and the metal ion complexes of the seventh and eighth aspects of the present invention, can be used for reducing inflammation, treating or preventing inflammation associated with arthritis (including osteoarthritis and rheumatoid arthritis), promoting hair growth, treating or preventing psoriasis, increasing blood flow, treating or preventing chilblains, treating or preventing varicose veins, treating a wound, promoting wound healing, treating or promoting healing of scar tissue (including scar tissue resulting from burns), treating burns, alleviating or reducing joint pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treat-ng or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease (MND; MND includes, for example, amyotrophic lateral sclerosis (ALS; also known as Lou Gehrig's Disease), primary lateral sclerosis (PLS), progressive muscular atrophy (FMA), progressive bulbar palsy (PEP) and pseudobulbar palsy), treating or preventing viral conditions, treating or preventing prion diseases (e.g. bovine spongiform encephalopathy (BSE), scrape, Creutzfeldt-Jakob disease (CJD) or its variant (vCJD), Gerstmann-Sträussler-Scheinker syndrome, fatal familial insomnia or kuru), treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases (e.g. multiple sclerosis, Parkinson's disease, Alzheimer's disease, dementia, transverse myelitis or epilepsy), treating or preventing asthma or other bronchial and/or respiratory conditions, treating or preventing osteoporosis, bone fractures or other bone conditions, treating or preventing eye cataracts or other eye conditions, or combinations thereof.

The metal ion complex (or mixture of metal ion complexes), or salt thereof, tautomer thereof or polymer thereof, is typically administered to a patient in the form of a composition comprising the metal ion complex (or mixture of metal ion complexes), or salt thereof, tautomer thereof or polymer thereof, and a pharmaceutically acceptable carrier.

Accordingly, the invention also provides a pharmaceutical composition comprising a metal ion complex (or mixture of metal ion complexes) obtained by the process of the first aspect of the present invention (or a pharmaceutically acceptable salt thereof, tautomer thereof or polymer thereof) and a pharmaceutically acceptable carrier. Similarly, the invention also provides a pharmaceutical composition comprising a metal ion complex (or mixture of metal ion complexes) of the seventh or eighth aspects of the present invention (or a pharmaceutically acceptable salt thereof, tautomer thereof or polymer thereof) and a pharmaceutically acceptable carrier.

In some embodiments, the metal ion complex (or mixture of metal ion complexes) of the seventh or eighth aspect of the present invention, or obtained by the process of the first aspect of the present invention (or a pharmaceutically acceptable salt thereof, tautomer thereof or polymer thereof) may be used in combination with one or more other therapeutically effective agents.

Accordingly, in some embodiments, the pharmaceutical composition may further comprise, or be administered in combination with, one or more other agents.

It will be understood that the combined administration of a metal ion complex (or mixture of metal ion complexes) of the seventh or eighth aspect of the present invention, or obtained by the process of the first aspect of the present invention, or a pharmaceutically acceptable salt thereof, tautomer thereof or polymer thereof, with the one or more other agents may be concurrent, sequential or separate administration.

The term "composition" encompasses formulations comprising the active ingredient with conventional carriers and excipients, including formulations comprising conventional carriers, excipients, creams, lotions etc. used for topical administration. The term "composition" also encompasses formulations with encapsulating materials as a carrier to provide a capsule in which the active ingredient (with or without other carriers) is surrounded by the encapsulation carrier. The carrier is "pharmaceutically acceptable" meaning that it is compatible with the other ingredients of the composition and is not deleterious to a subject. The compositions of the present invention may contain other agents or further active agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known the art of pharmaceutical formulation (See, for example, Remington: The Science and Practice of Pharmacy, 21st Ed., 2005, Lippincott Williams & Wilkins).

The pharmaceutical composition may be suitable for oral, rectal, nasal, topical (including buccal, sub lingual and slow release dermal patch), vaginal or parenteral (including intramuscular, subcutaneous and intravenous) administration or in a form suitable for administration by inhalation or insufflation.

The metal ion complex (or a mixture of metal ion complexes of the seventh and eighth aspects of the present invention (or a pharmaceutically acceptable salt thereof, tautomer thereof or polymer thereof or the metal ion complex (or the mixture of metal ion complex(es)) obtained by the process of the first aspect of the present invention (or a pharmaceutically acceptable salt thereof, tautomer thereof or polymer thereof), which are sometimes collectively referred to below as the "compounds of the invention", together with a conventional adjuvant, carrier, or diluent, may thus be placed into the form of pharmaceutical compositions and unit dosages thereof. The pharmaceutical composition may be a solid, such as a tablet or filled capsule, or a liquid such as solution, suspension, emulsion, elixir, or capsule filled with the same, for oral administration. The pharmaceutical composition may also be in the form of suppositories for rectal administration or in the form of sterile injectable solutions for parenteral (including subcutaneous) use. The pharmaceutical composition may also be in a form suitable for metered sterile nasal inhalation, such as a micronized powder diluted in a suitable excipient.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low molting wax, cocoa butter, and the like. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for injectable solutions or dispersions, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions may be prepared by incorporating the active ingredient in the required amount in the appropriate solvent with various other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze drying of a previously sterile filtered solution of the active ingredient plus any additional desired ingredients.

The compounds of the invention may be formulated into compositions suitable for oral administration, for example, with an inert diluent or with an assimilable edible carrier, or enclosed in hard or soft shell gelatin capsule, or compressed into tablets, or incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The amount of active compound in therapeutically useful compositions should be sufficient that a suitable dosage will be obtained. The tablets, troches, pills, capsules and the like may also contain one or more of the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac (or otherwise enteric coated), sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active ingredient(s) may be incorporated into sustained-release preparations and formulations, including those that allow specific delivery of the active ingredient to specific regions of the gut.

Aqueous solutions suitable for oral use may include suitable colorants, flavours, stabilising and thickening agents, as desired.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds of the invention may be formulated as ointments, creams or lotions, or as a transdermal patch or gels. Ointments and creams may, for example, be formulated with an aqueous or oily base with the addition of suitable thickening, emulsifying and/or gelling agents (e.g. emulsion of oil in water or emulsion of water in oil). Lotions may be formulated with an aqueous oily base and will in general also contain one or more emulsifying agents, stabilising agents, dispersing agents, suspending agents, thickening agents, colouring agents or preservatives (e.g. methyl paraben, propyl paraben, phenoxyethanol). Other agents may also be added to the topical formulations to provide other desired properties. For example, humectants, anti-oxidants, vitamins, colouring agents and fragrances may be added. Such additives may be natural (for example, plant extracts, animal-derived oils, vitamins), or may be synthetic (for example, surfactants or preservatives such as BHT).

As an example, a formulation for topical administration may comprise any or all of the following: Simmondsia Chinensis (Jojoba oil), glyceryl stearate, cetylstearyl alcohol, sodium stearoyl lactylate, stearic acid, glyceryl monostearate, glycerine, caprylic/capric triglyceride, PEG 20, sorbitan monolaurate, cocoa butter, triethanolamine, emu oil, shea butter, tocopheryl acetate (vitamin E), phenoxyethanol, ethylhexylglycerin, polyoxyethylene (20) sorbitan monooleate, acrylates/C10-30 alkyl acrylate crosspolymer, essential oil (e.g. lavender oil).

Formulations suitable for topical administration in the mouth include lozenges comprising active agent in a flavoured base, usually sucrose, maltitol, acacia or tragacanth; pastilles comprising the active ingredient in an inert base such as gelatin and glycerin or sucrose and acacia; and mouthwashes comprising the active ingredient in a suitable liquid carrier; buccal cavity patches or gels.

Solutions or suspensions for nasal administration may be applied directly to the nasal cavity by conventional means, for example with a dropper, pipette or spray. The formulations may be provided in single or multidose form. In the case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds of the invention may be encapsulated with cyclodextrins, or formulated with other agents expected to enhance delivery and retention in the nasal mucosa.

The invention also provides use of a metal ion complex (or mixture of metal ion complexes) of the seventh or eighth aspect of the present invention or obtained by the process of the first aspect of the present invention (or a pharmaceutically acceptable salt thereof, tautomer thereof or polymer thereof) in the manufacture of a medicament for reducing inflammation, treating or preventing inflammation associated with arthritis (including osteoarthritis and rheumatoid arthritis), promoting hair growth, treating or preventing psoriasis, increasing blood flow, treating or preventing chilblains, treating or preventing varicose veins, treating a wound, promoting wound healing, treating or promoting healing of scar tissue (including scar tissue resulting from burns), treating burns, alleviating or reducing joint pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease, treating or preventing viral conditions, treating or preventing prion diseases, treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases, treating or preventing asthma or other bronchial and/or respiratory conditions, treating or preventing osteoporosis, bone fractures or other bone conditions, treating or preventing eye cataracts or other eye conditions, or combinations thereof.

The invention also provides a method for reducing inflammation, treating or preventing inflammation associated with arthritis (including osteoarthritis and rheumatoid arthritis), promoting hair growth, treating or preventing psoriasis, increasing blood flow, treating or preventing chilblains, treating or preventing varicose veins, treating a wound, promoting wound healing, treating or promoting healing of scar tissue (including scar tissue resulting from burns), treating burns, alleviating or reducing joint pain, alleviating or reducing muscular pain, alleviating or reducing neuropathic or nerve pain, treating or preventing sinus inflammation, treating or preventing sinus pain, treating or preventing a bacterial infection, treating or preventing a fungal infection, treating or preventing eczema, treating or preventing wrinkles, treating or preventing bruises, treating or preventing joint degeneration, treating or preventing cartilage degeneration, treating or preventing acne, treating or preventing muscle damage, treating or preventing motor neuron disease, treating or preventing viral conditions, treating or preventing prion diseases, treating or preventing joint damage, treating or preventing tendon damage, treating or preventing onychoschizia (split nails), treating or preventing cancer, treating or preventing breast cancer, treating or preventing brain cancer, treating or preventing melanoma, treating or preventing basal cell carcinoma, treating or preventing squamous cell carcinoma, treating or preventing neuroinflammatory or neurodegenerative diseases, treating or preventing asthma or other bronchial and/or respiratory conditions, treating or preventing osteoporosis, bone fractures or other none conditions, treating or preventing eye cataracts or other eye conditions, or combinations thereof, in a human or animal, comprising administering to the human or animal a therapeutically effective amount of a metal ion complex (or mixture of metal ion complexes) of the seventh or eighth aspect of the present invention or obtained by the process of the first aspect of the present invention (or a pharmaceutically acceptable salt thereof, tautomer thereof and polymer thereof.

For example, for treatment or alleviation of inflammation, a topical formulation (e.g., a cream, lotion, spray or gel) comprising a metal ion complex or mixture of metal ion complexes according to the present invention may be applied to an inflamed area (e.g. one to three times per day) until inflammation is reduced. Treatment may continue for as long as necessary to reduce or continually alleviate inflammation.

As another example, for treatment or alleviation of pain including nerve or neurological pain, a topical formulation (e.g., a cream, lotion, spray or gel) comprising a metal ion complex or mixture of metal ion complexes according to the present invention may be applied to a painful area (e.g. one to three times per day) until the pain is reduced. Treatment may continue for as long as necessary to reduce or continually alleviate the pain.

For promoting hair regrowth, a topical formulation (e.g., a cream, lotion, gel, spray or shampoo) comprising a metal ion complex or mixture of metal ion complexes according to the present invention may be applied to the scalp (e.g. once or twice per day) for a period of time which is at least sufficient to stimulate or promote hair growth or regrowth.

As another example, for use as a sunscreen, a topical formulation (e.g., a cream, lotion, gel or spray) comprising a metal ion complex or mixture of metal ion complexes according to the present invention may be applied to an area of skin prior to exposure to the sun or UV radiation. Additional applications may be made as required.

As another example, for relief of sinus pain, a topical formulation (e.g., a cream, lotion, gel or spray) comprising a metal ion complex or mixture of metal ion complexes according to the present invention may be applied to an area of skin around the nose and/or under the eyes or across the forehead when pain starts, resulting in pain relief.

As another example, to reduce scarring, a topical formulation (e.g., a cream, lotion, gel or spray) comprising a metal ion complex or mixture of metal ion complexes according to the present invention may be applied, generally one to three times per day, e.g., twice a day, across the scar tissue with rubbing to work it into the scar tissue and surrounding skin.

As another example, for healing of bruising a topical formulation (e.g., a cream, lotion, gel or spray) comprising a metal ion complex or mixture of metal ion complexes according to the present invention may be applied to and around the bruised area (e.g. once a day) until bruising disappears.

As another example, for treatment of onychoschizia (split nails) a suitable formulation (e.g., a liquid, cream, tincture or lotion) comprising a metal ion complex or mixture of metal ion complexes according to the present invention may be applied (e.g. once a day) until the desired nail quality is attained.

As another example, for the treatment of skin conditions, such as acne, psoriasis or eczema, a suitable formulation (e.g., a liquid, cream, gel, spray, tincture or lotion) comprising a metal ion complex or mixture of metal ion complexes according to the present invention may be applied to the appropriate area in a manner similar to conventional therapies (e.g. from one to three times per day, and in some cases, twice per day).

As another example, for the treatment of neuroinflammatory conditions, such as multiple sclerosis, Parkinson's disease, Alzheimer's disease, dementia, transverse myelitis or epilepsy, a suitable formulation (e.g., a liquid, gel, topical spray, nasal spray, dermal or buccal cavity patch, or sublingual lozenge or tablet) comprising a metal ion complex or mixture of metal ion complexes according to the present invention may be applied to the appropriate area in a manner similar to conventional therapies (e.g. from one to three times per day, and in some cases, twice per day).

Dosages

The term "therapeutically effective amount" refers to the amount of a compound that will elicit the biological or medical response in a subject, tissue or cell that is being sought by the veterinarian, medical doctor or other clinician.

It will be understood that the therapeutically effective amount of a metal ion complex will depend upon a variety of factors including the activity of the specific complex(es) employed, the metabolic stability and length of action of that complex, the age, body weight, general health, sex and diet of the subject, the mode and time of administration, rate of excretion, drug combinations, and the severity of the particular condition.

It will further be understood that when the complexes of the invention are to be administered in combination with one or more other agents, or other active agents, the dosage forms and levels may be formulated for either concurrent, sequential or separate administration or a combination thereof.

EXAMPLES

The present invention is further described below by reference to the following non-limiting Examples.

Materials

Copper turnings: Sigma-Aldrich Pty Ltd, 12 Anella Avenue, Castle Hill, NSW 2154 Australia.

$H_2O_2$: Pedox Pty Ltd, 2 Swettenham Road Minto New South Wales 2566 Australia.

Disodium EDTA: Redox Pty Ltd, 2 Swettenham Road Minto New South Wales 2566 Australia.

Bulk Density

The metal used in the following Examples (copper) is relatively dense (density of about 8.9 g/cm$^3$). Both "freshly settled" and "tapped" bulk densities may be determined for the copper particles. The "freshly settled" bulk density and "tapped" bulk density can be determined by adding 100 g of the copper particles to a 200 ml measuring cylinder. The initial volume measured in the measuring cylinder is the "freshly settled" volume. The measuring cylinder is then picked up and dropped 3 times from a height of 2 cm onto a solid surface. The volume measured in the measuring cylinder at this stage is the "tapped" volume. The "tapped" bulk density can then be determined by the formula:

$$\text{"tapped" bulk density (in g/mL g/cm}^3\text{)} = \frac{100}{\text{"tapped" volume (in mL or g/cm}^3\text{)}}$$

For the Examples employing copper wire as the metal particles, there was no significant difference between the "freshly settled" and "tapped" bulk densities. The bulk density of the copper used in each of the Examples is set out in Table 1. The bulk densities specified in Table 1 are the "tapped" bulk density determined as described above.

Example 1

Quantities

| | |
|---|---|
| Cu (fine wire) | 10.0 g |
| $H_2O_2$ (50 wt. %, aq.) | 20.0 g |
| EDTA-Na$_2$ | 44.0 g |
| $H_2O$ | 80.0 g |

Method

Place the Cu fine wire in a 500 ml Pyrex beaker.
Add the EDTA powder to the beaker on top of the Cu fine wire.
Add the water to the beaker.
Add the $H_2O_2$ to the beaker and swirl to mix.

Results

Experiment continued for 10 days without any noticeable reaction except for some gas release from the base where the metal and undissolved EDTA lay. The liquid was bright blue and became increasingly so over the 10 days. Ambient temperature was approx. 20° C. This experiment was allowed to continue for 30 days. No noticeable changes or visible signs of reaction were observed.

Example 2

Quantities

| | |
|---|---|
| Cu (fine wire) | 7.0 g |
| $H_2O_2$ (50 wt. %, aq.) | 20.0 g |
| EDTA-Na$_2$ | 44.0 g |
| $H_2O$ | 80.0 g |

Method

As per Example 1

Results

Experiment continued for 10 days without any noticeable reaction except for some gas release from the base where the metal and undissolved EDTA lay. The liquid was bright blue and became increasingly so over the 10 days. Ambient temperature was approx. 20° C. This experiment was allowed to continue for 30 days. No noticeable charges or visible signs of reaction were observed.

The reactions in Examples 1 and 2 formed CuEDTA or some other "non-active" metal chelate.

It is believed that this is due to the ambient temperature and the ratio of Cu:EDTA:$H_2O_2$ not being conducive to the reaction proceeding to completion within the time frame used in the Examples.

Example 3

Quantities

| | |
|---|---|
| Cu (fine wire) | 96.0 g |
| $H_2O_2$ (50 wt. %, aq.) | 200.0 g |
| EDTA-Na$_2$ | 438.0 g |
| $H_2O$ | 800.0 g |

Method

Place the Cu fine wire in a 500 ml Pyrex beaker.
Add the EDTA powder to the beaker on top of the Cu fine wire.
Add the water to the beaker.
Add the $H_2O_2$ to the beaker and swirl to mix.

Results

Ambient temperature approximately 20° C. After 10 days a layer of approximately 1 cm of EDTA remains on the bottom of the reaction vessel. Small gas bubbles continue to emanate from the bottom of the reaction vessel seemingly at the metal/liquid interface. The liquid is bright blue. A further 30.0 g 50 wt. % aq. $H_2O_2$ (15 g $H_2O_2$) was added after 11 days.

Still no noticeable change in rate of reaction over the next 48 hours so added an additional 50.0 g 50 wt. % aq. $H_2O_2$ (25 g $H_2O_2$). This experiment was allowed to continue for a further 24 hours.

This last addition of $H_2O_2$ promoted a significantly more vigorous reaction, but did not result in the "exothermic final reaction". The resulting solution was bright blue which we believe is due to the presence of CuEDTA.

Example 4

Quantities

| | |
|---|---|
| Cu (fine wire) | 100.0 g |
| $H_2O_2$ (50 wt. %, aq.) | 200.0 g |
| EDTA-Na$_2$ | 200.0 g |
| $H_2O$ | 800.0 g |

Method

As per Example 1.

Results

After 12 hours the reaction mixture reached a critical point and an exothermic reaction rapidly ensued, causing the majority of the reaction mixture to "explode" out of the reaction vessel and into the safety container. During this final exothermic reaction, the mixture changed in colour from bright blue to a very dark, not transparent blue/green, "oily" looking liquid.

Example 5

Quantities

| | |
|---|---|
| Cu (fine wire) | 100.0 g |
| $H_2O_2$ (50 wt. %, aq.) | 200.0 g |
| EDTA-$Na_2$ | 200.0 g |
| $H_2O$ | 800.0 g |

Method

As per Example 1.

Results

Ambient temperatures were in the vicinity of 25° C.-30° C. During the reaction the reaction mixture got very hot. The reaction vessel was placed into a controlled temperature water bath at 35° C.

After 11 hours the reaction mixture reached a critical point and an exothermic reaction rapidly ensued and "boiled" over, equally as violently as Example 4.

Of the 100.0 g of Cu starting material, 69.0 g remained unreacted leading to the conclusion that 31.0 g was complexed. Equivalent of 31.0 g/L Cu.

Examples 6 to 15

Method

Used a similar method to that described above in Example 1, but with the reaction mixture heater in a heating mantle to 80° C. The reagents used are as specified in Table 1.

Results

In each of these Examples, the reaction went rapidly to completion and overflowed into the capture vessel. For example, in Example 13, the reaction took 13 minutes and considerable steam was released.

Example 16

Quantities

| | |
|---|---|
| Cu (turnings) | 200.0 g (Hot approx. 80° C.) |
| $H_2O_2$ (50 wt. %, aq.) | 132.0 g (Cold) |
| EDTA-$Na_2$ | 220.0 g (Cold) |
| $H_2O$ | 390.0 g (90° C.) |

Method

Place the Cu fine wire in a 5,000 ml Pyrex beaker and heat to approx. 80° C.

Add the EDTA powder to the beaker on top of the Cu turnings.

Add the hot (approx. 90° C.) water to the beaker.

Add the $H_2O_2$ to the beaker and swirl to mix.

Keep reaction mixture at approx. 80° C. without further agitation.

Results

The reaction went to completion, ending with a strongly exothermic reaction.

Of the 200.0 q of Cu starting material, 169.2 g remained unreacted leading to the conclusion that 30.8 g was complexed. Equivalent of 59.0 g/L Cu.

This experiment was repeated 4 further times with equivalent Cu complexed of 60.1 g/L, 58.4 g/L, 57.2 g/L and 5.35 g/L. Average 58.6 g/L.

Example 17

Quantities

| | |
|---|---|
| Cu (turnings) | 200 g |
| $H_2O_2$ (50 wt. %, aq.) | 132 g |
| EDTA-$Na_2$ | 220 g |
| $H_2O$ | 390 g |

Method

Place the Cu turnings in a Pyrex reaction vessel over a heating mantle.

Dissolve EDTA-$Na_2$ in water at 80° C. and decant the supersaturated solution of EDTA-Na, and add that solution to the Cu turnings.

Add the $H_2O_2$ to the reaction vessel and swirl to mix.

Keep reaction mixture at approx. 80° C. without further agitation.

Results

The reaction did not proceed to a strong exothermic stage, instead reaching only a weakly exothermic stage. The resulting mixture was clear blue, indicating the likely presence of CuEDTA.

Example 18

Quantities

| | |
|---|---|
| Cu (fine wire) | 1061.6 g |
| $H_2O_2$ (50 wt. %, aq.) | 700.6 g |
| EDTA-$Na_2$ | 1167.7 g |
| $H_2O$ | 2070.1 g |

Method

Place the Cu fine wire in an oven and heat to approx. 80° C.

Add the EDTA powder to the beaker on top of the Cu fine wire.

Add the hot (approx. 85° C.) water to the beaker.

Add the $H_2O_2$ to the beaker and swirl to mix.

Keep reaction mixture at approx. 85° C. without further agitation.

Results

The reaction went to completion, ending with a strongly exothermic reaction.

Of the 1061.6 g of Cu starting material, 720.0 g remained unreacted leading to the conclusion that 341.6 g was complexed. Equivalent of 47.98 g/L Cu.

In some of the Examples described above a red precipitate (presumably an oxide of copper) was observed to settle to the bottom of the reaction vessel and/or adhere to the walls of the vessel (and occurred both immediately and over time). This is easily separated and it is not apparent that this changes the activity of the desired copper ion complex.

TABLE 1

Summary of Results

| Example No. | Cu [mol] | Cu Type | Bulk density (g/cm³) | EDTA [mol] | 50 wt. % aq. H$_2$O$_2$ [mol] | Cu:EDTA:H$_2$O$_2$ (in mol equivalents) | Solid EDTA in contact with Cu | Temp | [Cu]$^\Delta$ (g/L) | HPLC A:B$^\dagger$ | Completion | Colour of solution at conclusion of experiment |
|---|---|---|---|---|---|---|---|---|---|---|---|---|
| 1 | 10 g [0.157] | Fine Wire | 1 | 44 g [0.118] | 20 g/10 g [0.294] | 1.33:1:2.49 | yes | ambient (~20° C.) | — | — | no | blue |
| 2 | 7 g [0.110] | Fine Wire | 1 | 44 g [0.118] | 20 g/10 g [0.294] | 0.93:1:2.49 | yes | ambient (~20° C.) | — | — | no | blue |
| 3 | 96 g [1.51] | Fine Wire | 1 | 438 g [1.17] | 280 g/140 g [4.12] | 1.29:1:3.52 | yes | ambient (~20° C.) | 35.40 | 16:84 | no | blue |
| 4 | 100 g [1.57] | Fine Wire | 1 | 200 g [0.534] | 200 g/100 g [2.94] | 2.94:1:5.51 | yes | ambient (~20° C.) | 25.20 | — | yes (exothermic reaction observed) | blue/green |
| 5 | 100 g [1.57] | Fine Wire | 1 | 200 g [0.534] | 200 g/100 g [2.94] | 2.94:1:5.51 | yes | ~25-35° C. | 31.00 | — | yes (exothermic reaction observed) | blue/green |
| 6 | 100 g [1.57] | Fine Wire | 1 | 250 g [0.668] | 200 g/100 g [2.94] | 2.35:1:4.40 | yes | heated (~80° C.) | 34.33 | — | yes (exothermic reaction observed) | blue/green |
| 7 | 100 g [1.57] | Coarse Wire | 2 | 200 g [0.534] | 200 g/100 g [2.94] | 2.94:1:5.51 | yes | heated (~80° C.) | 27.00 | — | yes (exothermic reaction observed) | blue/green |
| 8 | 40 g [0.630] | Coarse Wire | 2 | 200 g [0.534] | 200 g/100 g [2.94] | 1.18:1:5.51 | yes | heated (~80° C.) | 27.00 | 30:70 | yes (exothermic reaction observed) | blue/green |
| 9 | 200 g [3.15] | Coarse Wire | 2 | 1000 g [2.67] | 1000 g/500 g [14.70] | 1.18:1:5.51 | yes | | | | | |
| 10 | 20 g [0.315] | Coarse Wire | 2 | 100 g [0.267] | 100 g/50 g [1.47] | 1.18:1:5.51 | yes | | | | | |
| 11 | 41.2 g [0.648] | Coarse Wire | 2 | 219 g [0.585] | 100 g/50 g [1.47] | 1.11:1:2.51 | yes | | | | | |
| 12 | 100 g [1.57] | Turnings | 1.5 | 110 g [0.294] | 50 g/25 g [0.735] | 5.35:1:2.51 | yes | | | | | |
| 13 | 100 g [1.57] | Turnings | 1.5 | 110 g [0.294] | 50 g$^\S$/17.5 g [0.514] | 5.35:1:1.75 | yes | | | | | |
| 14 | 200 g [3.15] | Fine Wire | 1 | 220 g [0.588] | 110 g/55 g [1.617] | 5.35:1:2.75 | yes | | | | | |
| 15 | 600 g [9.44] | Turnings | 1.5 | 110 g [0.294] | 50 g/25 g [0.735] | 32.1:1:2.51 | yes | | | | | |
| 16 | 200 g [3.15] | Fine wire & Turnings (hot) | 1.25 | 220 g [0.588] | 132 g/66 g [1.94] | 5.35:1:3.30 | yes | | | | | |
| 17 | 200 g [3.15] | Turnings | 1.5 | 220 g [0.588] | 132 g/66 g [1.94] | 5.35:1:3.30 | no (EDTA solution) | | | | | |
| 18 | 1061.6 g [16.71] | Fine Wire | 1.5 | 1167.7 g [3.14] | 700.6 g/350.3 g [10.3] | 5.33:1:3.28 | yes | | | | | |

TABLE 1-continued

Summary of Results

| | | | | | |
|---|---|---|---|---|---|
| 9 | heated (~80° C.) | — | 38:62 | yes (exothermic reaction observed) | blue/green |
| 10 | heated (~80° C.) | 11.74 | 52:48 | yes (exothermic reaction observed) | blue/green |
| 11 | heated (~80° C.) | 14.40 | 16:84 | yes (exothermic reaction observed) | blue/green |
| 12 | heated (~80° C.) | 62.40 | 25:75 | yes (exothermic reaction observed) | blue/green |
| 13 | heated (~80° C.)§ | 58.80 | — | yes (exothermic reaction observed) | blue/green |
| 14 | heated (~80° C.) | 50.00 | 35:65 | yes (exothermic reaction observed) | blue/green |
| 15 | heated (~80° C.) | 57.60 | — | yes (exothermic reaction observed) | blue/green |
| 16 | heated (~80° C.) | 58.64 | 42:58 | yes (exothermic reaction observed) | blue/green |
| 17 | heated (~80° C.) | 23.00 | 15:85 | no | blue |
| 18 | heated (~80° C.) | — | 32:68 | yes (exothermic reaction observed) | blue/green |

ΔConcentration of Cu in solution at end of reaction based on recovered Cu starting material.
†Ratio of A:B as determined by HPLC, where A is the metal ion complex having a retention time of ~8 min and B is the metal ion complex having a retention time of ~18 min (Phenomenex Luna HILIC analytical column; 3 μm, 2 × 100 mm; 85:15 $CH_3CN$/ammonium formate buffer (0.1M, pH 4.3), 0.3 mL/min).
§35 wt. % $H_2O_2$ used in Example 13.
— Indicates the data was not recorded or not applicable.

Example 19—Characterisation of Metal Ion Complexes

A mixture of copper complexes was prepared using the method described above in Example 18.

Initial attempts to separate the mixture of copper complexes by HPLC (Biotage Isolera; DIOL 12 g Reverlis column; UV 300 nm; 85:15 $CH_3CN$/citrate buffer (0.1 M, pH 5.50), 30 ml/min) afforded various fractions containing copper complexes. For example, "Fraction 1", "Fraction 2" and "Fraction 6" were obtained, which were analysed independently (see, for example, $^1H$ NMR spectra in FIGS. 1, 2 and 3). However, the separation proved difficult in practice and characterisation was therefore subsequently performed on the mixture of copper complexes obtained using the method of Example 18 (without purification).

Example 18 created a mixture of copper complexes presenting as a dark blue/green liquid having a solids content of 42% and pH 6.5 (referred to herein as "Sample 19.1").

Sample 19.1 was dried (vacuum, 37.5° C., 24 h), affording a solid that was dark green and crystalline in appearance (referred to herein as "Sample 19.2"). Sample 19.2 was found to be highly hygroscopic, highly polar, highly soluble in water, and had limited (if any) solubility in other polar and non-polar solvents (such as ethanol, methanol, butanol, propanol, chloroform, dimethyl sulphoxide, pentane, propane, butane, hexane etc.).

Sample 19.1 and Sample 19.2 were subjected to various characterisation techniques. The results of some of these characterisation techniques are summarised below.

Analytical HPLC

Analytical HPLC was performed on Sample 19.1, indicating the presence of two major components. Component A (as referred to in Table 1 above) had a retention time of ~8 min and Component B (as referred to in Table 1 above) had a retention time of ~18 min (Phenomenex Luna HILIC analytical column; 3 μm, 2×100 mm; 85:15 $CH_3CN$/ammonium formate buffer (0.1 M, pH 4.3), 0.3 mL/min).

Infrared Spectroscopy

An infrared absorption spectrum of a sample obtained from Example 14 was recorded on a fourier transform spectrophotometer (Thermo Fisher Scientific; thin film), which showed peaks at 3250 and 1600 $cm^{-1}$, consistent with the presence of amino group(s) and carboxylic acid group(s).

$^1H$ NMR

Figure 2:
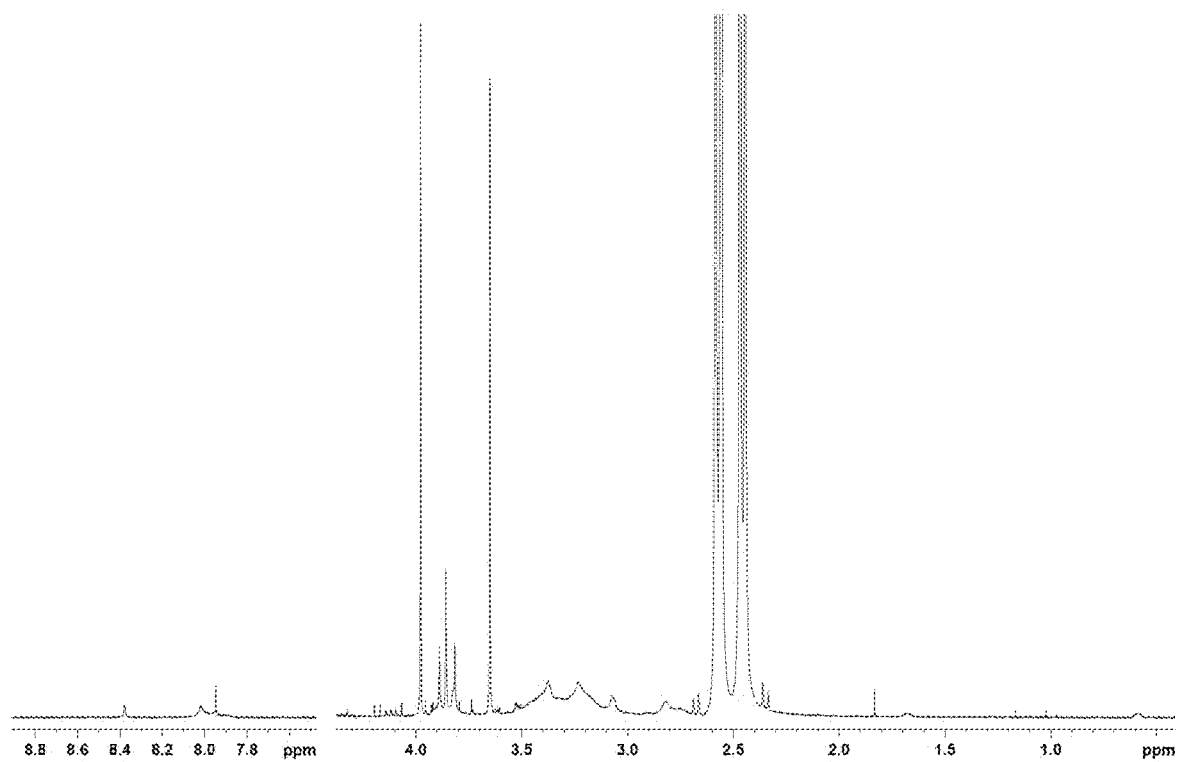
FIG. 2 is a 600 MHz $^1$H NMR spectrum of "Fraction 2" in $D_2O$ (as described in Example 19) plotted as signal intensity vs. chemical shift (ppm).
Figure 3:
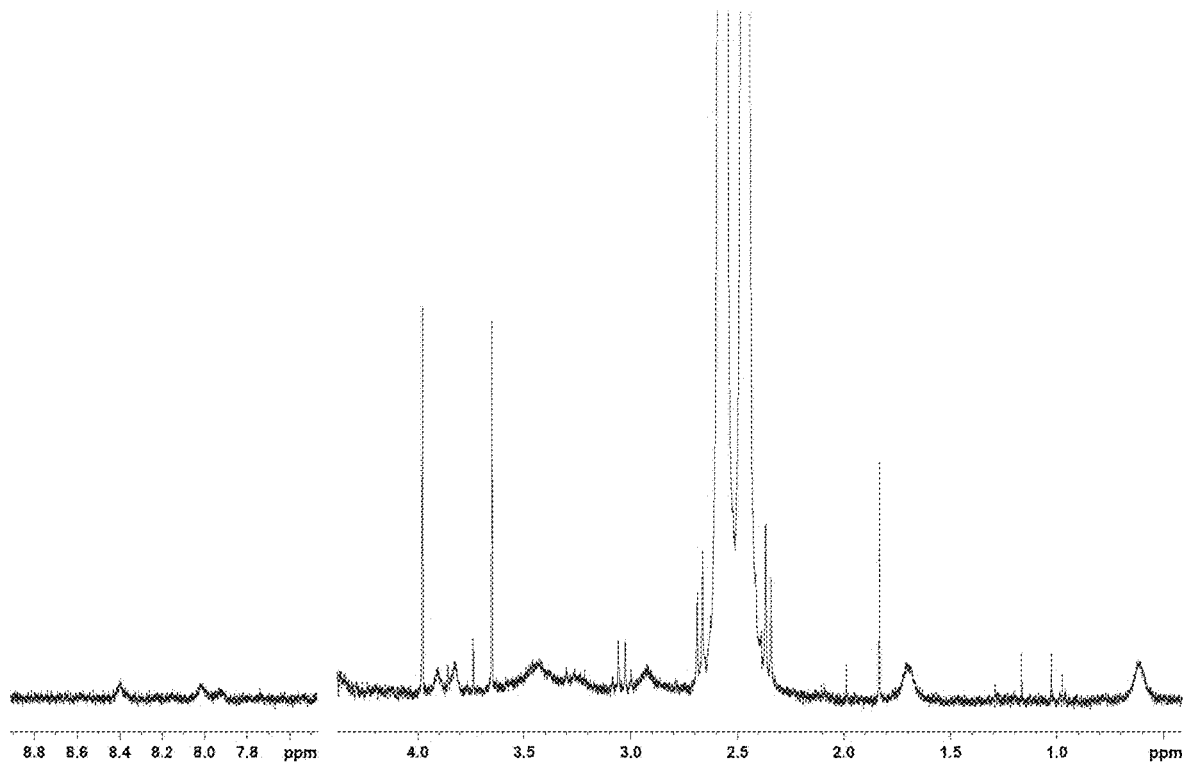
FIG. 3 is a 600 MHz $^1$H NMR spectrum of "Fraction 6" in $D_2O$ (as described in Example 19) plotted as signal intensity vs. chemical shift (ppm).
Figure 4:
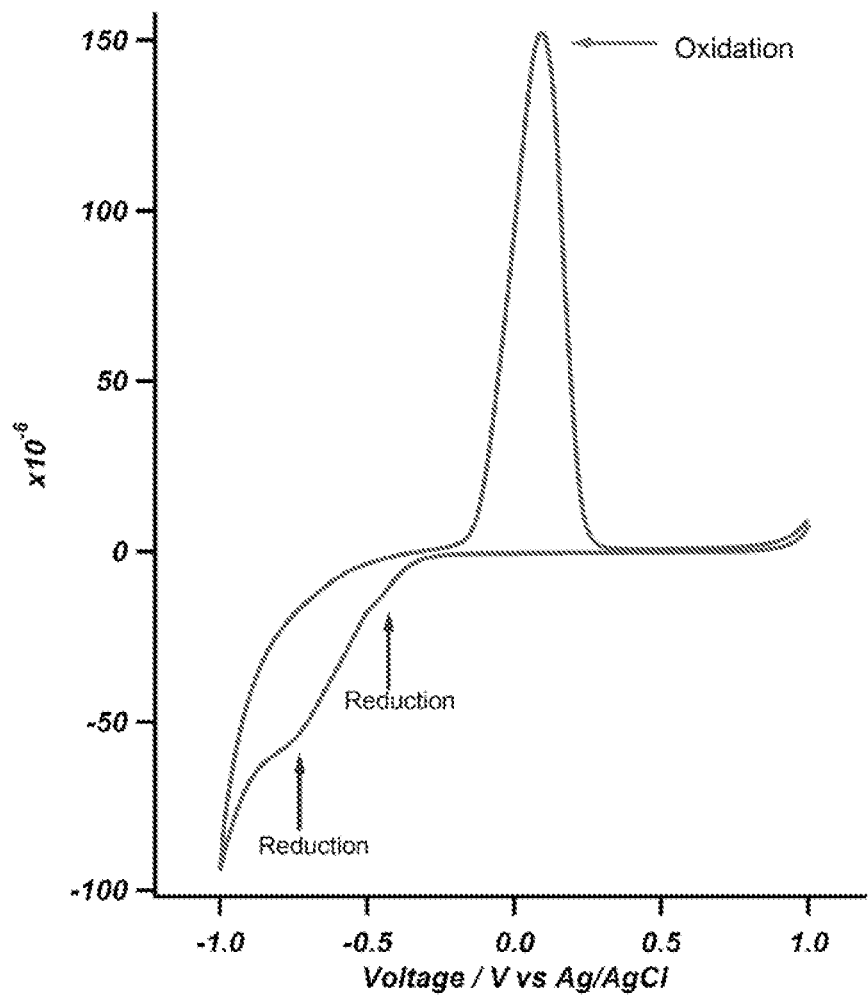
FIG. 4 is a cyclic voltammogram trace showing the current (in μA, i.e. $10^{-6}$ amps) vs potential (in V vs Ag/AgCl) of Sample 19.1 (as described in Example 19).

NMR spectra were recorded on a Bruker AV III 630 MHz spectrometer equipped with a BBFO probe. 1- and 2-dimensional NMR experiments were performed, including 1H-13C single and multiple bond correlation (HSQC and HMBC experiments, respectively) on three fractions obtained from the HPLC purification described above. H NMR spectra of Fraction 1, Fraction 2 and Fraction 6 are shown in FIGS. 1, 2 and 3, respectively.

The NMR spectra are consistent with functional groups present in the ligands of Formula (I) and Formula (II).

Cyclic Voltammetry Analysis

Sample 19.1 was subjected to cyclic voltammetry and differential pulse voltammetry. The sample was diluted 50 times in acetate buffer (pH 6.1). The Cyclic Voltammetry analysis indicated the copper to be in the +3 oxidation state. The cyclic voltammogram trace is shown in FIG. 3, which shows two reduction peaks and one oxidation peak, consistent with a $Cu^{3+}$ ion.

From the analysis of Samples 19.1 and 19.2, it was determined that Sample 19.1 contained copper complexes of Formula (III) and Formula (IV) (i.e. complexes of Formula (III) and Formula (IV) where M is $Cu^{2+}$ and/or $Cu^{3+}$).

Example 20—RT$^2$ Profiler PCR Array Gene Expression

In this study, 96 genes were profiled on 3 samples (Sample 19.1 and 2 controls) with the PAHS-014Z using the RT$^2$ Profiler PCR Array Gene Expression kit.

The RT$^2$ Profiler PCR Array is a highly reliable and sensitive gene expression profiling tool for analysing focused panels of genes in signal transduction, biological processes or disease research pathways using real-time PCR. The catalogued RT$^2$ Profiler PCR Array contains a list of the pathway-focused genes as well as five housekeeping (reference) genes on the array. In addition, the array contains a panel of controls to monitor genomic DNA contamination (GDC) as well as the first strand synthesis (RTC) and real-time PCR efficiency (PPC). The qPCR Assays used in PCR Arrays are laboratory-verified and optimized to work under standard conditions enabling a large number of genes to be assayed simultaneously.

Cataloged Arrays

1. Mature RNA was isolated using an RNA extraction kit according to the manufacturer's instructions.
2. RNA quality was determined using a spectrophotometer and was reverse transcribed using a cDNA conversion kit.
3. The cDNA was used on the real-time RT$^2$ Profiler PCR Array (QIAGEN, Cat. no. PAHS-014Z) in combination with RT$^2$ SYBR® Green qPCR Mastermix (Cat. no. 330529).

$C_T$ values were exported to a table that was uploaded to the data analysis web portal at http://www.qiagen.com/geneglobe. $C_T$ values were normalized based on an automatic selection from full panel of reference genes.

The data analysis web portal calculates fold change/regulation using the delta delta $C_T$ method. In this method, delta $C_T$ is calculated between the gene of interest (GOI) and an average of reference genes (HKG), followed by delta-delta $C_T$ calculations (delta $C_T$ (Test Group)–delta $C_T$ (Control Group)). Fold Change is then calculated using the formula $2^{(-\text{delta delta } C_T)}$.

Fold-Change (i.e. $2^{(-\text{delta delta } C_T)}$) may also be expressed as the normalized gene expression ($2^{(-\text{Delta } C_1)}$) in the Test Sample divided by the normalized gene expression ($2^{(-\text{Delta } C_T)}$) in the Control Sample. Fold-Regulation represents fold-change results in a biologically meaningful way. Fold-change values greater than one indicate a positive- or an up-regulation, wherein the fold-regulation is equal to the fold-change. Fold-change values less than one indicate a negative or down-regulation, wherein the fold-regulation is the negative inverse of the fold-change. Results of this study are summarised in Table 2 below.

TABLE 2

Summary of results from RT$^2$ Profiler PCR Array Gene Expression and Associated Diseases

| Gene | **Fold Up/Down Regulation | Associated Pathway | Disease Class Associated with Gene/Pathway | Examples of Diseases/Conditions/Functions Associated with Gene/Pathway and/or Disease Class |
|---|---|---|---|---|
| HES5 | +19.81 | Notch Signaling | Tissue Regeneration and Cell Survival | Muscle and Skin Regeneration, Brain Repair, Tumour Suppression - including forebrain tumours, Connective Tissue (including ligament and tendon) Regeneration, Cell Survival (Normal Cells), Impact Injuries |
| HMOX1 | +12.68 | Heme Oxygenase Signaling Hypoxia Signalling | Inflammatory Diseases and Conditions, including Vascular, Joint and Brain Analgesia/Pain Relief | Osteoarthritis, Burns (including sunburn), Sprains and Strains Neuropathic Pain, Hand and Foot Syndrome, Pain from Impact Injuries |
| SERPINE1 | +7.56 | HIF-1 Signaling p53 Signaling Hippo Signaling | Inherited Thrombophilia and Blood Disorders | Thromboses including Deep Vein Thrombosis, Pulmonary Embolism |
| ACSL5 | +4.59 | PPAR Signaling | Brain Function Brain Cancer | Increases Brain Function and Brain Glucose, Decreases Inflammation, Decreases Oxidative Stress, Mediates Fatty-Acid-Induced Glioma cell growth |
| TNF | +4.53 | TNF Signaling | Neuroinflammatory Diseases Cancer Inflammatory Diseases | Alzheimer's Disease, Parkinsons Disease, ALS, Cancer, Major Depression, Psoriasis and Inflammatory Bowel Disease |
| GADD45B | +4.51 | p38/JNK Signaling | Cancer Inflammatory Diseases Senescence | All Cancers - activates immune Response to Cancer Dementia Age related diseases including senility |
| SQSTM1 | +4.16 | NF-κB Signaling | Cancer Senescence/Neuronal Inflammatory | All Cancers through activation of Stem Cells and MND, MS, Parkinsons |
| BMP4 | +4.12 | Hedgehog Signaling | Cancer Inflammatory Diseases Senescence | Breast Cancer Inhibition and Inhibition of Metastasis Acute Inflammatory Lung Conditions including Asthma, COPD Age-related Macular Degeneration (AMD) |

TABLE 2-continued

Summary of results from RT² Profiler PCR Array Gene Expression and Associated Diseases

| Gene | **Fold Up/Down Regulation | Associated Pathway | Disease Class Associated with Gene/Pathway | Examples of Diseases/Conditions/Functions Associated with Gene/Pathway and/or Disease Class |
|---|---|---|---|---|
| SORBS1 | +3.07 | PPAR Signaling<br>Insulin Signaling | Trauma induced damage<br>Diabetes and Obesity | Muscle, heart, bone, connective tissues including tendons and ligament damage<br>Insulin Resistance in Type 2 Diabetes |
| FAS | −163.83 | p53 Signaling | Cancer | Glioblastoma multiforme, lung (adenocarcinoma), colorectal, advanced gastric, pancreatic, ovarian, breast, and prostate. |
| WNT5A | −105.13 | Hedgehog Signaling | Cancer | All Cancers - promotes motility and proliferation, including Glioblastoma |
| ID1 | −70.04 | Notch Signaling | Cancer | All cancers - inhibits DNA binding, promotes chemoresistance<br>Non Small-Cell-Lung Cancer, Gastric Cancer, Breast Cancer and is a promoter of Metastasis, Prostate Cancer, Melanoma, Glioblastoma, DIPG |
| CEBPD | −51.88 | JAK/STAT Signaling | Cancer | Suppresses tumours |
| OLR1 | −39.26 | PPAR Signaling<br>NF-κB Signaling | Cancer | Non small, cell lung cancer, Gastric Cancer, Breast Cancer and is a promoter of Metastiasis, Prostate Cancer, Melanoma, Glioblastoma |
| DAB2 | −33.73 | Wnt Signaling | Cancer<br>Neuroinflammatory Diseases | Melanoma, Colorectal, Cervical, Lung and Stomach Cancer<br>Multiple Sclerosis, Parkinsons Disease |
| CCND2 | −32.95 | p53/JAK-STAT Signaling | Cancer | Lung cancers, Thyroid Cancers, Adenocarcinomas of Cervix, Squamous Cell Carcinoma |
| ACTB | −29.26 | Rap1 Signaling<br>Hippo Signaling<br>Thyroid Hormone Signaling<br>Oxytocin Signaling | Cancer | Colorectal, Ovarian, Endometrial, Testicular, Breast, Urothelial, Pancreatic and Liver and Lymphomas |
| CDKN1B (p27Kip1) | −27.17 | ErbB Signaling<br>HIF-1 Signaling<br>FoxO Signaling<br>PI3k-Akt Signaling | Cancer | Glioma, Melanoma |
| PCNA | −25.87 | RAD6 Signaling | Cancer | All Cancers |
| CPT2 | −24 | PPAR Signaling | Cancer | Hepatocellular Carcinomas, Colorectal Cancers |
| MYC | −22.57 | Myc Signaling | Cancer | Burkitt Lymphoma and Carcinoma of the cervix, colon, breast, lung and stomach |
| CCND1 | −22.53 | PI3K/AKT Signaling | Cancer | Non-small cell lung cancers, head and neck squamous cell, carcinomas, pancreatic carcinomas, bladder cancer, pituitary adenomas, breast carcinoma, ER + breast cancer and hormone therapy resistance in breast cancer, B mantle cell lymphoma |
| NQO1 | −22.36 | NF-κB Signaling<br>AP-1 Signaling<br>p53 | Cancer | Colon, breast, pancreas, ovaries and thyroid, and melanoma |
| BCL2L1 | −22.01 | Ras signaling<br>FF-κB Signaling<br>PI3K-Akt Signaling<br>Jak-STAT Signaling | Cancer | her2-recepcor negative breast cancer, colorectal cancer, non-small-cell lung cancer subtypes, adenocarcinoma, squamous cell carcinoma.<br>Potent, inhibitor of cell death. Inhibits activation of caspases. Appears to regulate cell death by blocking the voltage-dependent anion channel (VDAC) by binding to it and preventing the release of the caspase activator, CYC1, from the mitochondrial membrane. Also acts as a regulator of G2 checkpoint and progression to cytokinesis during mitosis. |
| EMP1 | −21.39 | Src Kinase Signaling<br>PI3K/AKT Signaling | Cancer<br>Lung Conditions | Endobronchial lipoma and bronchial neoplasm, asthma, non-small-cell lung cancer |
| SLC27A4 | −17.72 | PPAR Signaling | Intestinal and Obesity Related Conditions | Insulin Resistance Syndrome, Obesity |
| BBC3 | −17.2 | p53 Signaling<br>ERK Signaling | Cancer | Glioma, colorectal, breast, endometrial, skin, gastric and liver cancers |
| BCL2 | −16.51 | ErbB Signaling<br>Ras Signaling<br>cGMP-PKG Signaling<br>cAMP Signaling<br>PI3K-Akt Signaling<br>VEGF Signaling<br>Apoptosis Signaling | Cancer<br>Psychological Conditions<br>Autoimmune function | Melanoma, breast, prostate, chronic lymphocytic leukemia, and lung cancer;<br>Schizophrenia; and<br>Autoimmunity |
| STAT1 | −16.48 | IFN Signaling | Cancer | Renal, gastric, cervical, ovarian and breast cancers |
| EGFR | −15.22 | EGFR Signaling | Cancer<br>Skin Conditions | Glioblastoma multiforme, lung (adenocarcinoma), colorectal, advanced gastric, pancreatic, ovarian, breast, and prostate.<br>Psoriasis, eczema and atherosclerosis |

TABLE 2-continued

Summary of results from RT² Profiler PCR Array Gene Expression and Associated Diseases

| Gene | **Fold Up/Down Regulation | Associated Pathway | Disease Class Associated with Gene/Pathway | Examples of Diseases/Conditions/Functions Associated with Gene/Pathway and/or Disease Class |
|---|---|---|---|---|
| ACSL4 | −13.44 | PPAR Signaling Adipocytokine signaling | Cancer Neurological Disorders Neuronal Development | Breast cancer - both triple and quadruple negative types Mental retardation and other neurodegenerative diseases |
| PTCH1 | −12.56 | Hedgehog Signaling | Cancer | Medulloblastoma, nevoid basal cell carcinoma syndrome, esophageal squamous cell carcinoma, trichoepitheliomas, transitional cell carcinomas of the bladder |
| HPRT1 | −11.36 | Purine metabolism Drug metabolism - other enzymes | Metabolic Diseases | Obesity, Hyperthyroidism, Hypothyroidism, Diabetes I & II |

**Fold-Change (2^(−Delta Delta CT)) is the normalized gene expression (2^(−Delta CT)) in the Test Sample divided the normalized gene expression (2^(−Delta CT)) in the Control Sample. Fold-Regulation represents fold-change results in a biologically meaningful way. Fold-change values greater than one indicates a positive- or an up-regulation, and the fold-regulation is equal to the fold-change. Fold-change values less than one indicate a negative or down-regulation, and the fold-regulation is the negative inverse of the fold-change.

The up- or down-regulation of the genes referred to in Table 2 can be used to treat or prevent diseases in humans or animals where the up or down regulation of the gene would be beneficial. For example, the copper complex up-regulates the HES5 gene +19.81 fold. The up-regulation of this gene would be expected to promote tissue regeneration, improving healing time etc. Similarly, the copper complex significantly down-regulates the FAS gene (−163.83), a gene implicated in the progression of cancers.

The copper complexes of Sample 19.1 mimic the activities of the human GHK-Cu tripeptide, but with advantages over both the native GHK Tripeptide and the GHK-Cu Tripeptide. For example, Pickart et al. (Oxidative Medicine and Cellular Longevity; Volume 2012, Article ID 324832, doi: 10.115/2012/324832) report that in equivalent studies using mRNA, GHK showed a 1.9 fold increase in activity over the control, whereas the copper complexes of Sample 19.1 showed a 19.81 fold increase in activity of the HES5 gene. This gene influences tissue regeneration through expression of the FGF2 cytokine. This in turn enhances muscle and skin regeneration, brain repair, tumour suppression—including forebrain tumours, connective tissue (including ligament and tendon) regeneration, and cell survival (normal cells). The implication of this result is that this copper complex may provide enhanced fibroblast growth over the body's own naturally occurring GHK and GHK-Ca. This is important in skin, muscle and other tissue repair. Further, Pickart et al. report that it has not yet been determined whether or not the body's GHK Tripeptide or GHK-Cu Tripeptide cross the blood brain barrier. However, the inventors have evidence that at least some of the present copper complexes may rapidly cross the blood-brain barrier, at a race that can be considered as "actively transported" by the body's own mechanisms. Pickart et al. further report that human GHK Tripeptide does not down-regulate any gene pathways, whereas the inventors have found that copper complexes of the present invention may significantly down-regulate, amongst others, the p53 (FAS gene) by ~160 told (as mentioned above), the Hedgehog Pathway (WNT5A gene) by ~105 fold and the Notch (ID-1 gene) by ~70 fold. The down-regulation of these particular pathway genes has implications for cancer treatment across a range of cancer types. The inventors have demonstrated anti-cancer activity of the copper complexes against glioblastoma, melanoma, breast cancer and basal cell carcinoma, with treatment showing limited, if any, degradation of normal healthy cells run in parallel. Further, such copper complexes up-regulate a number of important regenerative and protective genes, including the Notch Pathway (HES5 gene; which shows ~20 fold up-regulation), the HO1 Pathway (HMOX1 gene; which shows ~13 fold up-regulation) and the NFkB, PPAR and Hedgehog Pathways (which show an ~4 fold up-regulation). Together these genes are responsible for (among others): muscle regeneration, brain repair, tumor suppression, tissue repair, cell survival. (normal cells), anti-inflammatory activity, anti-oxidant activity, pain relief, TNF activation, brain glucose/function, neuron regeneration, skin regeneration, hair regrowth and bone regeneration.

Example 21—Cell Lines

Sample 19.1 was assessed for activity in various cell lines, as detailed below.

Melanoma Cell Line

Sample 19.1 was assayed against the melanoma cell lines MM200 and MelRMu using a CellTiter 96® AQueous One Solution Cell Proliferation Assay by Promega.

Protocol:
1. Thaw the CellTiter 96® AQueous One Solution Reagent (approximately 90 minutes at room temperature, or 10 minutes in a water bath at 37° C., to completely thaw 20 ml of reagent).
2. Pipette 20 µl of CellTiter 96® AQueous One Solution Reagent into each well of the 96-well assay plate containing the samples in 100 µl of culture medium.
3. Incubate the plate at 37° C. for 1-4 hours in a humidified, 5% $CO_2$ atmosphere.
   (Note: To measure the amount of soluble formazan produced by cellular reduction of MTS, proceed immediately to Step 4. Alternatively, add 25 µl of 10% SDS to each well to stop the reaction in order to measure absorbance at a later stage; SDS-treated plates may be stored protected from light in a humidified chamber at room temperature for up to 18 hours.)
4. Record the absorbance at 490 nm using a 96-well olate reader.

Figure 5:
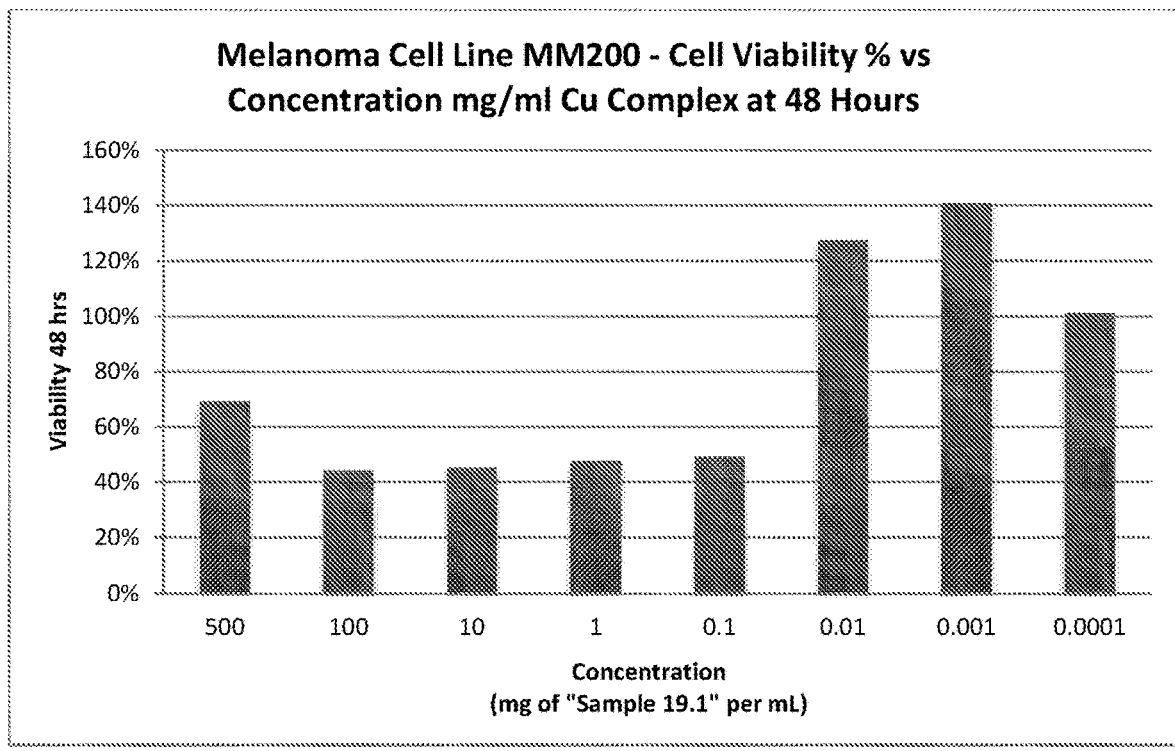
FIG. 5 is a graphical representation showing the viability (relative to untreated cells) of MM200 cells 48 h after treatment with Sample 19.1 (as described in Example 19) at different concentrations. This is a summary of the results of the melanoma cell line assay using MM200 cells as described in Example 21.
Figure 6:
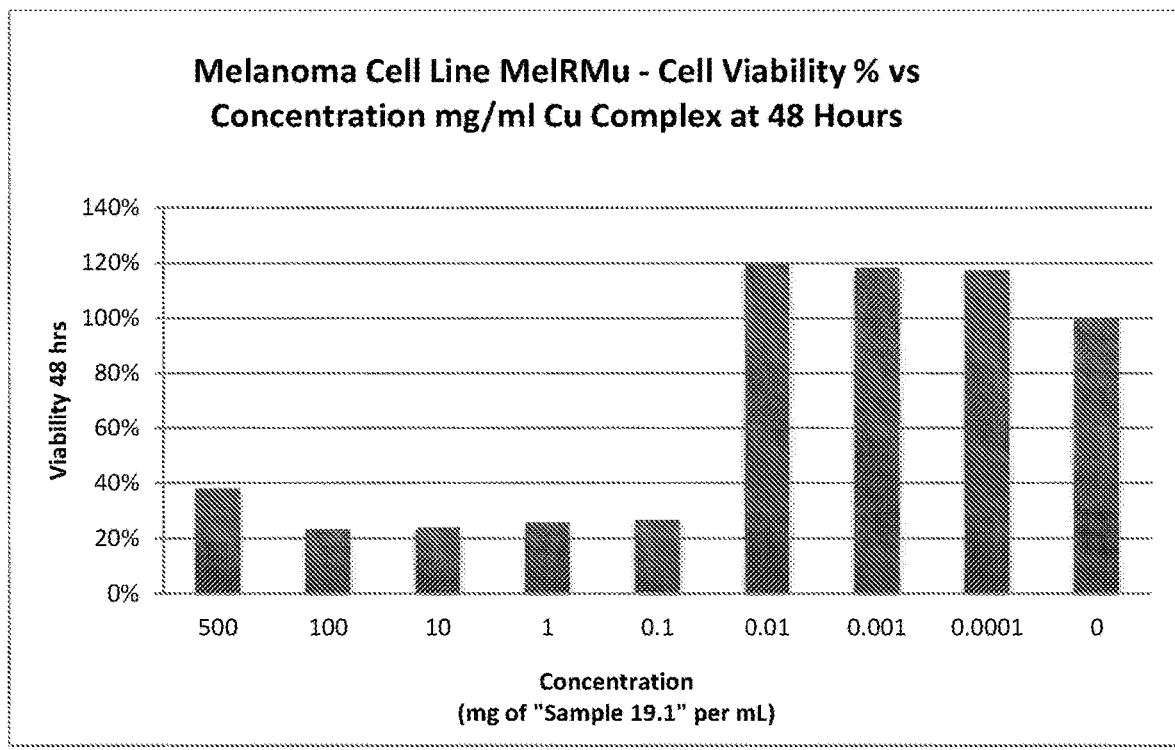
FIG. 6 is a graphical representation showing the viability (relative to untreated cells) of MelRMu cells 48 h after treatment with Sample 19.1 (as described in Example 19) at different concentrations. This is a summary of the results of the melanoma cell line assay using MelRMu cells as described in Example 21.

The results of the assay against MM200 cells are summarised in the graph shown in FIG. 5 and the results of the assay against MelRMu cells are summarised in the graph shown in FIG. 6.

These results demonstrate that at a concentration of 0.1 mg/ml (~44.3 micro molar) 50.8% and 73.3% respectively of the melanoma cells were killed after 48 hours. These results demonstrate that the copper complex mixture has activity against melanoma cell lines.

Breast Cancer Cell Line

Sample 19.1 was assayed against the breast cancer cell lines MCF7 (luminal/estrogen-positive breast cancer cells) and MDA-MB-231 (basal/hormone independent breast cancer cells) using a CellTiter 96® AQueous One Solution Cell Proliferation Assay by Promega.

Protocol:
1. Thaw the CellTiter 96® AQueous One Solution Reagent (approximately 90 minutes at room temperature, or 10 minutes in a water bath at 37° C., to completely thaw 20 ml of reagent).
2. Pipette 20 µl of CellTiter 96® AQueous One Solution Reagent into each well of the 96-well assay plate containing the samples in 100 µl of culture medium.
3. Incubate the plate at 37° C. for 1-4 hours in a humidified, 5% $CO_2$ atmosphere.
   (Note: To measure the amount of soluble formazan produced by cellular reduction of MTS, proceed immediately to Step 4. Alternatively, add 25 µl of 10% SDS to each well to stop the reaction in order to measure absorbance at a later stage; SDS-treated plates may be stored protected from light in a humidified chamber at room temperature for up to 18 hours.)
4. Record the absorbance at 490 nm using a 96-well plate reader.

Figure 7:
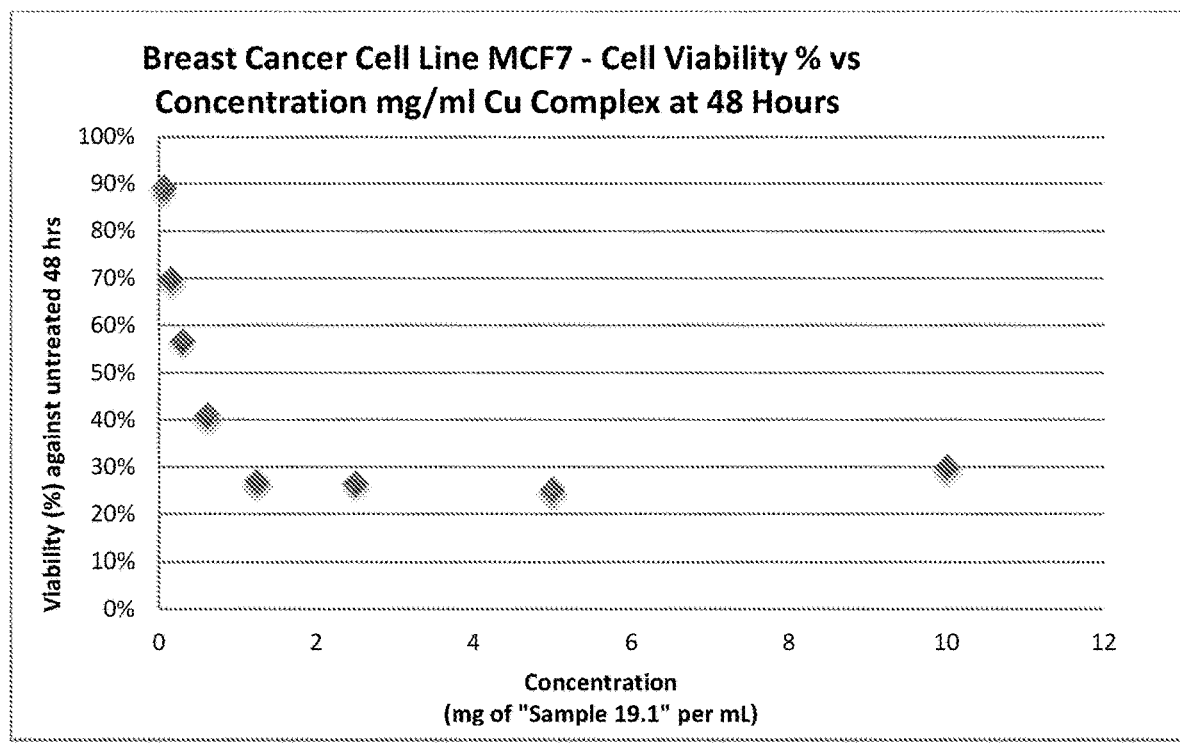
FIG. 7 is a graphical representation showing the viability (relative to untreated cells) of MCF7 cells 48 h after treatment with Sample 19.1 (as described in Example 19) at different concentrations. This is a summary of the results of the breast cancer cell line assay using MCF7 cells as described in Example 21.
Figure 8:
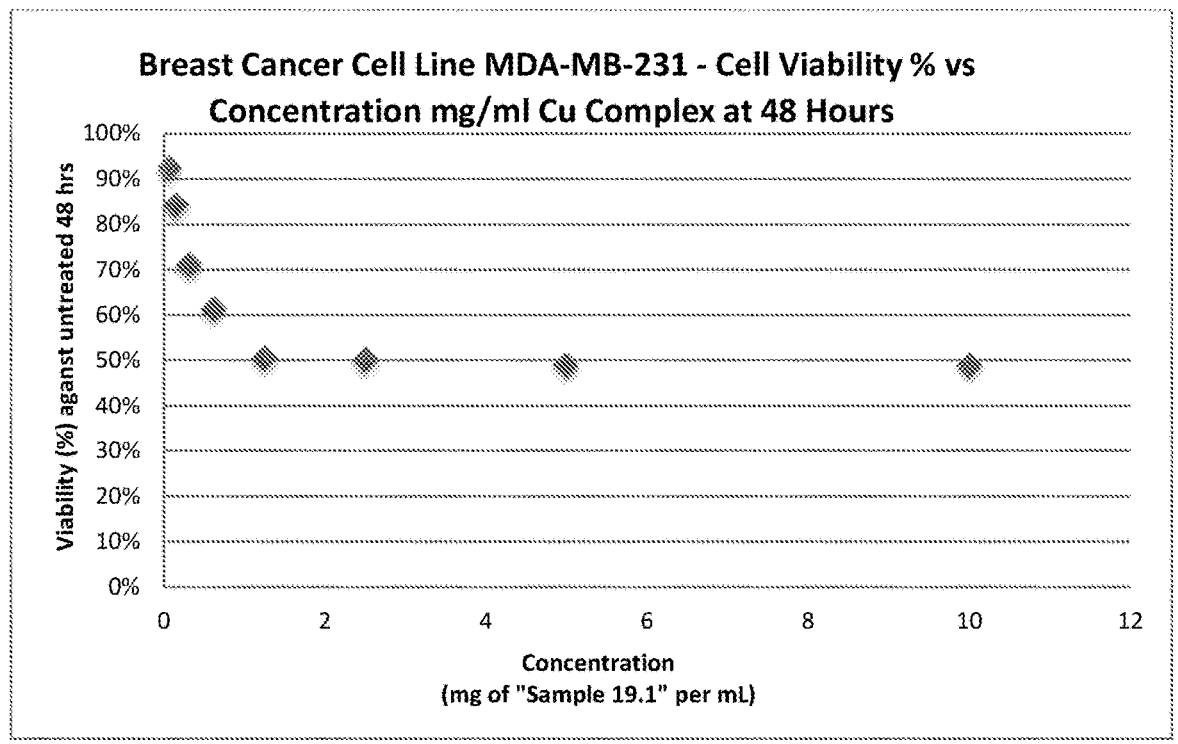
FIG. 8 is a graphical representation showing the viability (relative to untreated cells) of MEA MB 231 cells 48 h after treatment with Sample 19.1 (as described in Example 19) at different concentrations. This is a summary of the results of the breast cancer cell line assay using MUA-MB-231 cells as described in Example 21.

The results of the assay against MCF7 cells are summarised in the graph shown in FIG. 7a/b and the results of the assay against MDA-MB-231 cells are summarised in the graph shown in FIG. 8a/b.

These results demonstrate that the LD50 for the copper complex mixture against MCF7 is ~250 micromolar and the LD50 against MDA-MB-231 cells is ~2.2 millimolar. These results demonstrate that the copper complex mixture has activity against breast cancer cell lines.

Human Glioblastoma Cell Line

Sample 19.1 was assayed against the human glioblastoma cell lines U87MG and T95G (using Primary Foetal Astrocytes as control) using the following protocol:
   Cells were seeded in 96 well plates the day before treatment at pre-optimized concentrations (1.5×10^4 cells per 96 well plate for T98G, U87MG, and primary astrocytes).
   Cells were then treated with varying concentrations of Sample 19.1 (0, 0.025, 0.05, 0.1, 0.2, 0.3, 0.5 mg/ml), and a final concentration of 1× Peal Time Glo reagents (Promega).
   Cells were incubated and readings of cell metabolism taken at 24 and 48 h.
   Cell metabolism (death) was measured as a % of untreated cells and blanked against a no cell background control for each concentration of Sample 19.1 to remove any background luminescence from the compound.

Figure 9:
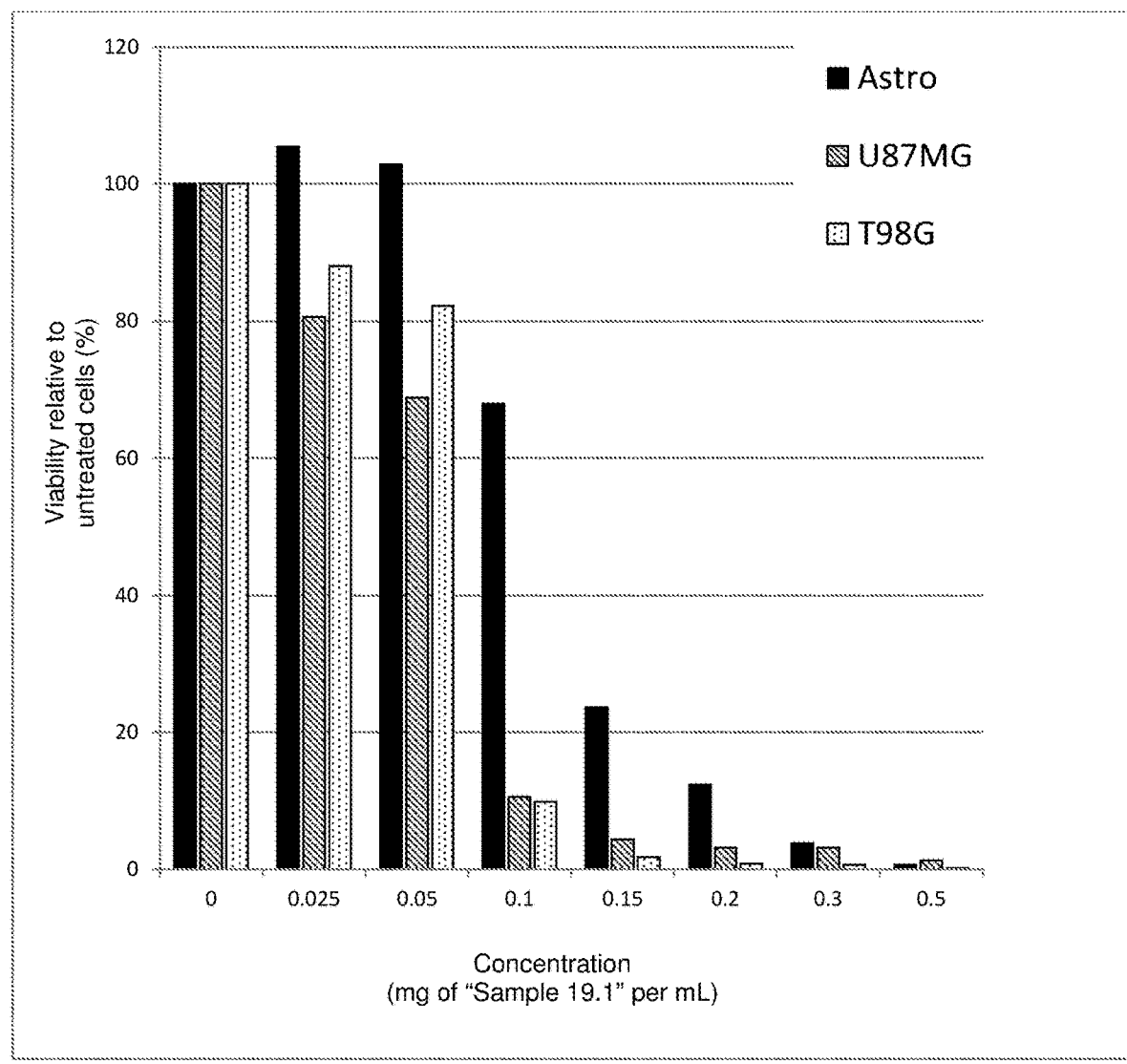
FIG. 9 is a graphical representation showing the viability (relative to untreated cells) of Primary Foetal Astrocyte, U87MG and T98G cells 48 h after treatment with Sample 19.1 (as described in Example 19) at different concentrations. This is a summary of the results of the human glioblastoma cell line assay using U87MG and T98G cells (with Primary Foetal Astrocyte cells as control) as described in Example 21.

The results of these assays are summarised in the graph shown in FIG. 9.

The results of these assays demonstrate that after 48 hours at a concentration of 0.1 mg/ml (~44.3 micro molar) only 9.86% of the glioblastoma cells survived whilst 68.0% of the Primary Foetal Astrocytes survived. These results demonstrate that the copper complex mixture has activity against human glioblastoma cell lines.

Example 22

Copper ion complexes prepared by the method described above in Example 18 (using copper, EDTA and hydrogen peroxide) were formulated into two topical formulations. The first formulation was prepared as a cream. This formulation was an oil-in-water emulsion containing 0.95% w/w of the copper complex (on a dry weight basis). The second formulation was prepared as a lotion, which was water based and contained 2.10% w/w of the copper complex (on a dry weight basis)

Treatment of Neuropathic Pain 62 year old female suffering long term (5 years) neuropathic pain post chemotherapy and radiation therapy for the treatment of breast cancer. After topical application of the lotion formulation, significant relief was experienced for approximately 7 hours. Repeated applications continued to provide significant relief of neuropathic pain.

63 year old male suffering long term (5 years) neuropathic pain post resection of bowel, chemotherapy and radiation therapy for the treatment of metastatic lung cancer. After topical application of the lotion formulation, significant relief was experienced for approximately 7 hours. Repeated applications continued to provide significant relief of neuropathic pain.

Treatment of Joint Injury 60 year old male suffering damaged shoulder from bicycle accident. Very limited movement and significant pain. After topical application of the cream formulation to the shoulder, immediate pain relief was experienced and full range of motion was returned within 7 days (compared to the year predicted by the treating physician).

Treatment of Hand and Foot Syndrome 62 year old male suffering from severe Hand and Foot Syndrome (HFS) as a result of long term (5 years) chemotherapy and radiation therapy. After topical application of the cream formulation to the affected areas (hands and feet), immediate relief of previously untreatable HFS was experienced. Pain was reduced in both hands and feet almost immediately. With longer term use (following treatment 4 times per day for 4 weeks) feeling returned to fingers and hands.

Treatment of Impact injury 68 year old female had left hand injured by jamming in car door. Immediate high level acute pain, swelling and significant bruising ensued. The lotion formulation was topically applied to the affected area immediately after injury, then half hourly for 4 hours then three hourly thereafter. Resulted in immediate pain relief, and overnight, the swelling, pain and bruising completely dissipated.

Treatment of Basal Cell Carcinoma

A 57 year old male with a basal cell carcinoma on his right forearm. The cream formulation was topically applied to the lesion and an adhesive bandage placed over the carcinoma. Cream was reapplied and the bandage was changed every 24 hours. The size and appearance of the carcinoma was visually examined every 24 hours. Over 3 weeks of treatment, the size of the carcinoma reduced and after 3 weeks of treatment, the carcinoma had been completely resolved with no visible scarring.

Treatment of Burns

A 37 year old female with a burn to her left forearm was treated by topical application of the cream formulation to the burnt area immediately after receiving the burn, then as the pain returned over a period of 2 weeks. The topical application of the cream formulation resulted in significant pain relief and after 2 weeks of treatment, the burn had healed with no scarring.

It is to be understood that, it any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A metal ion complex comprising a ligand of Formula (I) or Formula (II)

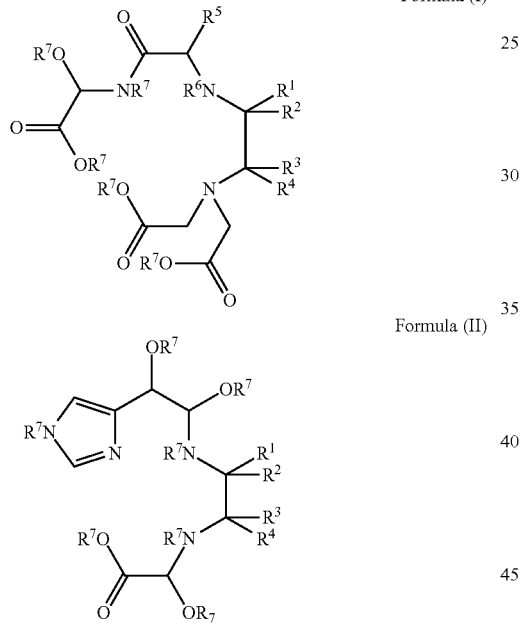

Formula (I)

Formula (II)

wherein
$R^1$ is H and $R^2$ is H or OH, or $R^1$ and $R^2$ together with the carbon atom to which they are attached form a carbonyl (C=O);
$R^3$ is H and $R^4$ is H or OH, or $R^3$ and $R^4$ together with the carbon atom to which they are attached form a carbonyl (C=O);
$R^5$ is —CH(OR$^7$)CH$_2$OR$^7$ or —CH$_2$CO$_2$R$^7$ and $R^6$ is absent or H, or $R^5$ is H and $R^6$ is —CH(OR$^7$)CH$_2$OR$^7$ or —CH$_2$CO$_2$R$^7$; and
each $R^7$ is independently absent or H;
or a salt thereof, tautomer thereof or polymer thereof.

2. The metal ion complex according to claim 1, wherein the ligand is of Formula (I), or a salt thereof, tautomer thereof or polymer thereof.

3. The metal ion complex according to claim 2, wherein $R^5$ is —CH(OR$^7$)CH$_2$OR$^7$ or —CH$_2$CO$_2$R$^7$ and $R^6$ is absent or H, or a salt thereof, tautomer thereof or polymer thereof.

4. The metal ion complex according to claim 3, wherein the ligand is of Formula (Ia)

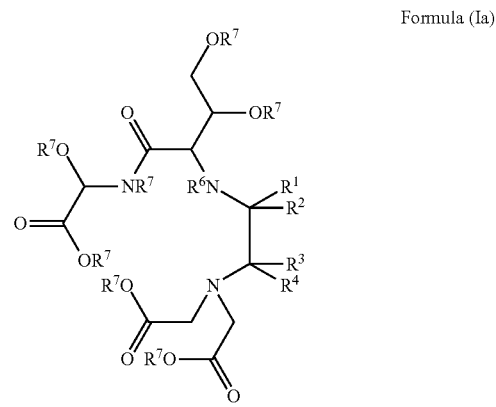

Formula (Ia)

wherein
$R^1$ is H and $R^2$ is OH, or $R^1$ and $R^2$ together with the carbon atom to which they are attached form a carbonyl (C=O);
$R^3$ is H and $R^4$ is OH, or $R^3$ and $R^4$ together with the carbon atom to which they are attached form a carbonyl (C=O);
$R^6$ is absent or H; and
each $R^7$ is independently absent or H;
or a salt thereof, tautomer thereof or polymer thereof.

5. The metal ion complex according to claim 4, wherein the ligand is of Formula (Ib)

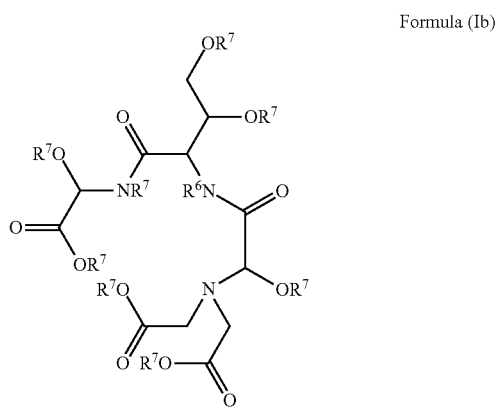

Formula (Ib)

wherein
$R^6$ is absent or H; and
each $R^7$ is independently absent or H;
or a salt thereof, tautomer thereof or polymer thereof.

6. The metal ion complex according to claim 1, wherein the ligand is of Formula (II), or a salt thereof, tautomer thereof or polymer thereof.

7. The metal ion complex according to claim 6, wherein the ligand is of Formula (IIa)

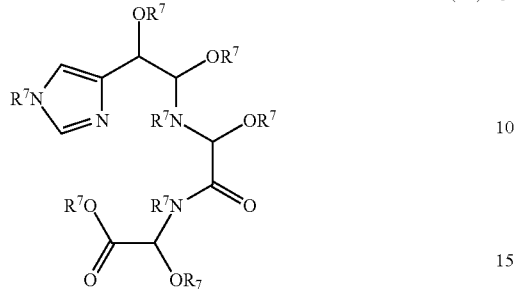

Formula (IIa)

wherein
each $R^7$ is independently absent or H;
or a salt thereof, tautomer thereof or polymer thereof.

8. The metal ion complex according to claim 1, comprising $Cu^{2+}$, $Cu^{3+}$ or a mixture of $Cu^{2+}$ and $Cu^{3+}$.

9. A composition comprising a metal ion complex or a mixture of metal ion complexes according claim 1, or a salt thereof, tautomer thereof or polymer thereof.

10. A formulation for topical administration comprising a metal ion complex or a mixture of metal ion complexes according to claim 1, or a salt thereof, tautomer thereof or polymer thereof.

* * * * *